United States Patent
Hasegawa et al.

(10) Patent No.: US 6,413,995 B1
(45) Date of Patent: Jul. 2, 2002

(54) CINNAMAMIDE DERIVATIVES AND DRUG COMPOSITIONS CONTAINING THE SAME

(75) Inventors: Yoshihiro Hasegawa; Shouichirou Shindou; Tomohisa Hattori; Tatsuhiro Obata; Fumiko Horiuchi; Hiroyuki Hayakawa; Hiroaki Kumazawa, all of Ibaraki (JP)

(73) Assignee: Tsumura & Co. (JP)

( * ) Notice: Subject to any disclaimer, the term of this patent is extended or adjusted under 35 U.S.C. 154(b) by 0 days.

(21) Appl. No.: 09/856,419

(22) PCT Filed: Jan. 11, 2000

(86) PCT No.: PCT/JP00/00082

§ 371 (c)(1),
(2), (4) Date: May 21, 2001

(87) PCT Pub. No.: WO00/42013

PCT Pub. Date: Jul. 20, 2000

(30) Foreign Application Priority Data

Jan. 11, 1999 (JP) .......................................... 11-004384

(51) Int. Cl.$^7$ ........................ C07D 213/40; A61K 31/44
(52) U.S. Cl. ........................................ 514/357; 546/336
(58) Field of Search ............................. 546/336; 514/357

(56) References Cited

U.S. PATENT DOCUMENTS 5,246,948 A    9/1993  Takatani et al. ............. 514/342

*Primary Examiner*—Zinna Northington Davis
(74) *Attorney, Agent, or Firm*—Fish & Richardson, P.C.

(57) ABSTRACT

The invention relates to cinnamamide derivatives having the following formula

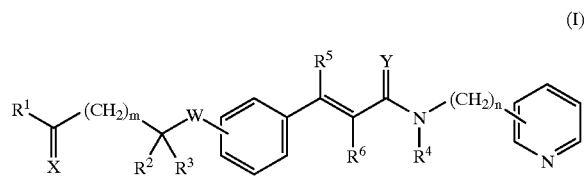

(I)

wherein
$R^1$ represents a hydroxyl group, a $C_{1-6}$-alkoxy group, an arylalkoxy group or a substituted or unsubstituted amino group;
$R^2$ and $R^3$ are same or different, each of which represents a hydrogen atom, a halogen atom or a $C_{1-4}$-alkyl group;
$R^4$ represents a hydrogen atom or a $C_{1-6}$-alkyl group;
$R^5$ represents a hydrogen atom, a $C_{1-6}$-alkyl group or an aryl group;
$R^6$ represents a hydrogen atom, a $C_{1-6}$-alkyl group, a cyano group or a $C_{1-6}$-alkoxy-carbonyl group;
W represents an oxygen atom, a sulfur atom, an imino group, a methylene group, a hydroxymethylene group or a carbonyl group;
X and Y are same or different, each of which represents an oxygen atom or a sulfur atom;
m represents an integer of 0 to 2;
n represents an integer of 1 to 3; and
when m is 0, a group: —$C(R^2)(R^3)$—W— may represent a vinylene group;
or a pharmaceutically acceptable salt thereof; and a pharmaceutical composition containing the above compound, in particular, an immunomodulatory agent and a prophylactic or therapeutic agent for nephrotic syndrome, circulatory disorders or respiratory diseases.

10 Claims, No Drawings

CINNAMAMIDE DERIVATIVES AND DRUG COMPOSITIONS CONTAINING THE SAME

This application is a 35 USC §371 of PCT/JP00/0082 filed on Jan. 11, 2000, which in turn claims the benefit of Japanese Application No. 4384/1999 filed on Jan. 11, 1999.

TECHNICAL FIELD

The present invention relates to cinnamamide derivatives and pharmaceutical compositions containing them. In particular, the present invention relates to an immunomodulatory agent and/or a prophylactic or therapeutic agent for nephrotic syndrome, circulatory disorders or respiratory diseases.

BACKGROUND ART

Interleukin 12 (IL-12) is currently known to play an important role in the differentiation of $CD4^+$ T lymphocytes into Th1 cells, and is also suggested to be a relevant to diseases associated with cellular immunity. Interleukin 6 (IL-6) is also known to induce cell growth of various cell types, as well as B cell growth and differentiation. On the contrary, Interleukin 10 (IL-10) is reported to have an inhibitory activity against cellular immunity. It is pointed out that IL-10 is relevant to diseases resulting from suppressed immunity. Accordingly, compounds which control the production of IL-6, IL-10 and IL-12 may be revolutionary new drugs that are expected to be effective in the treatment of diseases including autoimmune diseases resulting from excessive immunity (e.g., nephrotic syndrome, immunological rejection in transplantation, rheumatism, allergy), diabetes, liver disorders and tumors.

Since thromboxane $A_2$, which is produced in platelets, the lungs and the like, has strong platelet aggregation and smooth muscle constrictor activities, the regulation of thromboxane $A_2$ production influences blood pressure, bronchial asthma and/or blood coagulation. Accordingly, compounds which inhibit thromboxane $A_2$ synthase may be revolutionary new drugs that are expected to be effective for circulatory disorders (e.g., ischemic heart disease, thromboembolic disorder, disorder of cerebral circulation) and respiratory diseases (e.g., asthma).

Steroids are used as a first-choice drug for the treatment of nephrotic syndrome, but there is a problem that steroids cause disturbances in growth because nephrotic syndrome is often found in children. Cyclosporine is used for the treatment of intractable nephrosis, but cyclosporine is required to be administered while monitoring its blood level because it causes renal disorders including decreased renal function and hypertension. Under these circumstances, it is also desirable to develop an effective and less toxic therapeutic agent for nephrotic syndrome in the medical aspect.

DISCLOSURE OF THE INVENTION

An object of the present invention is to provide novel cinnamamide derivatives and pharmaceutical compositions containing them, in particular, to provide an immunomodulatory agent and a prophylactic or therapeutic agent for nephrotic syndrome, circulatory disorders or respiratory diseases.

The present invention encompasses the following embodiments.
(1) A cinnamamide derivative having the following formula (I):

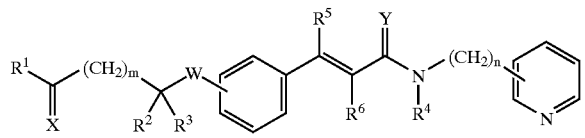

wherein
R$^1$ represents a hydroxyl group, a $C_{1-6}$-alkoxy group, an arylalkoxy group or a substituted or unsubstituted amino group;
R$^2$ and R$^3$ are same or different, each of which represents a hydrogen atom, a halogen atom or a $C_{1-4}$-alkyl group;
R$^4$ represents a hydrogen atom or a $C_{1-6}$-alkyl group;
R$^5$ represents a hydrogen atom, a $C_{1-6}$-alkyl group or an aryl group;
R$^6$ represents a hydrogen atom, a $C_{1-6}$-alkyl group, a cyano group or a $C_{1-6}$-alkoxy-carbonyl group;
W represents an oxygen atom, a sulfur atom, an imino group, a methylene group, a hydroxymethylene group (—CH(OH)—) or a carbonyl group (—CO—);
X and Y are same or different, each of which represents an oxygen atom or a sulfur atom;
m represents an integer of 0 to 2;
n represents an integer of 1 to 3; and
when m is 0, a group: —C(R$^2$)(R$^3$)—W— may represent a vinylene group (—CH=CH—);
or a pharmaceutically acceptable salt thereof.
(2) The cinnamamide derivative or pharmaceutically acceptable salt thereof according to (1) above, wherein the substituted amino group mentioned for R$^1$ is substituted with one or two groups selected from a substituted or unsubstituted $C_{1-6}$-alkyl group, a substituted or unsubstituted $C_{3-6}$-cycloalkyl group, a substituted or unsubstituted $C_{1-6}$-alkoxy group and a hydroxyl group; or is a cyclic amino group.
(3) A pharmaceutical composition, which comprises as an active ingredient the cinnamamide derivative or pharmaceutically acceptable salt thereof according to (1) or (2) above.
(4) An immunomodulatory agent, which comprises as an active ingredient the cinnamamide derivative or pharmaceutically acceptable salt thereof according to (1) or (2) above.
(5) A prophylactic or therapeutic agent for nephrotic syndrome, which comprises as an active ingredient the cinnamamide derivative or pharmaceutically acceptable salt thereof according to (1) or (2) above.
(6) A prophylactic or therapeutic agent for circulatory disorders, which comprises as an active ingredient the cinnamamide derivative or pharmaceutically acceptable salt thereof according to (1) or (2) above.
(7) A prophylactic or therapeutic agent for respiratory diseases, which comprises as an active ingredient the cinnamamide derivative or pharmaceutically acceptable salt thereof according to (1) or (2) above.

In the above formula (I), a $C_{1-6}$-alkoxy group mentioned for R$^1$ includes a linear or branched $C_{1-6}$-alkoxy group such as methoxy, ethoxy, n-propoxy, isopropoxy, n-butoxy, isobutoxy, sec-butoxy, t-butoxy, n-pentyloxy, isopentyloxy and n-hexyloxy. An arylalkoxy group mentioned for R$^1$ includes a $C_{1-3}$-alkoxy group substituted with a substituted or unsubstituted aryl group (e.g., phenyl, p-methoxyphenyl, tolyl, naphthyl), for example, benzyloxy and phenethyloxy.

An amino group mentioned for $R^1$ may be substituted with at least one group selected from a substituted or unsubstituted $C_{1-6}$-alkyl group, a substituted or unsubstituted $C_{3-6}$-cycloalkyl group, a substituted or unsubstituted $C_{1-6}$-alkoxy group and a hydroxyl group. This amino group may also be a cyclic amino group. A $C_{1-6}$-alkyl group used as a substituent on the above amino group includes a linear or branched $C_{1-6}$-alkyl group such as methyl, ethyl, n-propyl, isopropyl, n-butyl, isobutyl, sec-butyl, t-butyl, n-pentyl, isopentyl and hexyl. Such a $C_{1-6}$-alkyl group may further be substituted with at least one group selected from, for example, a $C_{1-6}$-alkoxy group (e.g., methoxy, ethoxy), a heterocyclic group (e.g., pyridyl, furyl), an aryl group (e.g., phenyl, p-methoxyphenyl, tolyl, naphthyl), an arylthio group (e.g., phenylthio, p-methoxyphenylthio, tolylthio, naphthylthio) and a $C_{1-6}$-alkoxy-carbonyl group (e.g., methoxycarbonyl, ethoxy-carbonyl).

A $C_{3-6}$-cycloalkyl group used as a substituent on the above amino group includes cyclopropyl, cyclobutyl, cyclopentyl and cyclohexyl. Such a $C_{3-6}$-cycloalkyl group may further be substituted with at least one group selected from, for example, a $C_{1-6}$-alkoxy group (e.g., methoxy, ethoxy), a heterocyclic group (e.g., pyridyl, furyl), an aryl group (e.g., phenyl, p-methoxyphenyl, tolyl, naphthyl), an arylthio group (e.g., phenylthio, p-methoxyphenylthio, tolylthio, naphthylthio) and a $C_{1-6}$-alkoxy-carbonyl group (e.g., methoxycarbonyl, ethoxycarbonyl).

A $C_{1-6}$-alkoxy group used as a substituent on the above amino group includes a linear or branched $C_{1-6}$-alkoxy group such as methoxy, ethoxy, n-propoxy, isopropoxy, n-butoxy, isobutoxy, sec-butoxy, t-butoxy, n-pentyloxy, isopentyloxy and n-hexyloxy. Such a $C_{1-6}$-alkoxy group may further be substituted with at least one group selected from, for example, a $C_{1-6}$-alkoxy group (e.g., methoxy, ethoxy), a heterocyclic group (e.g., pyridyl, furyl), an aryl group (e.g., phenyl, p-methoxyphenyl, tolyl, naphthyl), an arylthio group (e.g., phenylthio, p-methoxyphenylthio, tolylthio, naphthylthio) and a $C_{1-6}$-alkoxy-carbonyl group (e.g., methoxycarbonyl, ethoxycarbonyl).

An amino group substituted with a substituted or unsubstituted $C_{1-6}$-alkyl group includes methylamino, ethylamino, n-propylamino, isopropylamino, n-hexylamino, dimethylamino, diethylamino, benzylamino, picolylamino, 2-methoxyethylamino, 2-phenylthioethylamino, and ethoxycarbonylmethylamino. An amino group substituted with a substituted or unsubstituted $C_{3-6}$-cycloalkyl group includes cyclopentylamino and cyclohexylamino. An amino group substituted with a substituted or unsubstituted $C_{1-6}$-alkoxy group includes methoxyamino. An amino group substituted with a hydroxyl group includes hydroxylamino. An amino group substituted with several substitutents includes N-methoxy-N-methylamino and N-hydroxy-N-methylamino. A cyclic amino group includes morpholino and piperidino.

In the above formula (I), a $C_{1-4}$-alkyl group mentioned for $R^2$ or $R^3$ includes a linear or branched $C_{1-6}$-alkyl group such as methyl, ethyl, n-propyl, isopropyl, n-butyl, isobutyl, sec-butyl and t-butyl. A $C_{1-6}$-alkyl group mentioned for $R^4$, $R^5$ or $R^6$ includes a linear or branched $C_{1-6}$-alkyl group such as methyl, ethyl, n-propyl, isopropyl, n-butyl, isobutyl, sec-butyl, t-butyl, n-pentyl, isopentyl and hexyl.

A halogen atom mentioned for $R^2$ or $R^3$ includes a fluorine atom, a chlorine atom, a bromine atom and an iodine atom.

An aryl group mentioned for $R^5$ includes phenyl, p-methoxyphenyl, tolyl and naphthyl.

A $C_{1-6}$-alkoxy-carbonyl mentioned for $R^6$ includes a carbonyl group substituted with a linear or branched $C_{1-6}$- alkoxy group, such as methoxycarbonyl, ethoxycarbonyl, n-propoxycarbonyl, isopropoxycarbonyl, n-butoxycarbonyl, isobutoxycarbonyl, sec-butoxycarbonyl, t-butoxycarbonyl, n-pentyloxycarbonyl, isopentyloxycarbonyl and n-hexyloxycarbonyl.

In the above formula (I), a pyridyl group may be any one of 2-pyridyl, 3-pyridyl or 4-pyridyl.

In the present invention, a pharmaceutically acceptable salt may be an inorganic acid salt including hydrochloride, sulfate, hydrobromide, nitrate and phosphate, or an organic acid salt including trifluoroacetate, tartrate, citrate, malate, maleate, fumarate, methansulfonate, benzenesulfonate and toluenesulfonate. Some compounds may take the form of hydrates, which naturally fall within the scope of the present invention.

Compound (I) of the present invention also has cis- and trans-stereoisomers, as is apparent from its chemical structure. These stereoisomers naturally fall within the scope of the present invention.

Compound (I) of the present invention may be prepared by various methods. Representative methods (1) to (4) are presented below:

Method (1) Where W and Y are Oxygen Atoms in Formula (I):

Compound (I) of the present invention may be prepared by reacting a carboxylic acid of formula (II):

$$R^7O\text{—}Ar\text{—}C(R^5)\!=\!C(R^6)\text{—}COOH \qquad (II)$$

wherein
$R^7O$—Ar represents a phenyl group which is substituted with a hydroxyl group having an easily removable protecting group $R^7$; and
$R^5$ and $R^6$ are as defined above;

or reactive derivatives thereof, with an amine of formula (III):

$$R^4\text{—}NH\text{—}(CH_2)_n\text{—}Py \qquad (III)$$

wherein
Py represents a 2-pyridyl, 3-pyridyl or 4-pyridyl group; and
$R^4$ and n are as defined above;

to give an amide derivative of formula (IV):

$$R^7O\text{—}Ar\text{—}C(R^5)\!=\!C(R^6)\text{—}CON(R^4)\text{—}(CH_2)_n\text{—}Py \qquad (IV)$$

wherein
$R^4$, $R^5$, $R^6$, $R^7O$—Ar, Py and n are as defined above;
and then removing the protecting group $R^7$ from the hydroxyl group to provide a compound of formula (V):

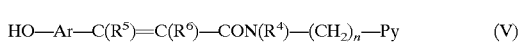

$$HO\text{—}Ar\text{—}C(R^5)\!=\!C(R^6)\text{—}CON(R^4)\text{—}(CH_2)_n\text{—}Py \qquad (V)$$

wherein
HO—Ar represents a phenyl group substituted with a hydroxyl group; and
$R^4$, $R^5$, $R^6$, Py and n are as defined above;

followed by alkylation of compound (V) in the presence of a base using a halide of formula (VI):

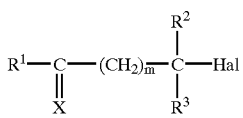

(VI)

wherein

Hal represents a halogen atom such as a chlorine or bromine atom; and $R^1$, $R^2$, $R^3$, X and m are as defined above.

Method (2) Where Y is an Oxygen Atom in Formula (I):

Compound (I) may be prepared by reacting a carboxylic acid of formula (VII):

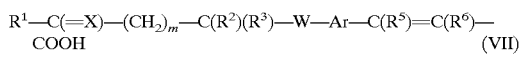

$$R^1-C(=X)-(CH_2)_m-C(R^2)(R^3)-W-Ar-C(R^5)=C(R^6)-COOH \quad (VII)$$

wherein

Ar represents a phenyl group; and $R^1$, $R^2$, $R^3$, $R^5$, $R^6$, m and W are as defined above;

or reactive derivatives thereof, with an amine of formula (III):

$$R^4-NH-(CH_2)_n-Py \quad (III)$$

wherein

Py, $R^4$ and n are as defined above.

Cinnamic acid derivatives (II) and (VII) and amine compound (III), which are used as starting materials, are commercially available or may be prepared in a general manner.

When compound (I) has a carbonyl group as group W, such a compound may be prepared by oxidizing a compound prepared from the above method (2), in which W is a hydroxymethylene group (—CH(OH)—), using manganese dioxide or pyridinium dichromate or by Swern oxidation.

When compound (II) or (VII) is provided in the form of carboxylic acid, in particular, these reactions are preferably carried out in the presence of a condensation agent such as dicyclohexylcarbodiimide, N,N'-carbonyldiimidazole, 1-hydroxy-benzotriazole, N-hydroxysuccinimide, diethylphosphoryl cyanide, diphenylphosphoryl azide. It is particularly advantageous to use diethylphosphoryl cyanide in combination with triethylamine. Reactive derivatives of compound (II) or (VII) include acid halides, acid anhydrides, mixed acid anhydrides and the like.

These reactions are preferably carried out in an inert solvent, including organic solvents such as tetrahydrofuran, dimethylformamide and dichloromethane, in particular, under anhydrous conditions. The reactions may be carried out at any temperature, in general, under ice-cold conditions up to under ambient conditions. The reaction time is generally in the range of 0.5 to 20 hours. Following the reaction, the product of interest may be isolated in a general manner.

As a protecting group $R^7$ for a hydroxyl group in compound (II), an acetyl group, a methoxymethyl group, a methoxyethoxymethyl group, a benzyl group or the like may be used. These protecting groups may be removed in suitable manners for their nature, in general, by acid hydrolysis.

The subsequent alkylation reaction may use an inert solvent appropriately selected from dimethylformamide, tetrahydrofuran, dioxane, acetone, acetonitrile and the like. A base that can be used in the alkylation reaction includes inorganic bases such as sodium hydride and potassium carbonate, as well as organic bases such as triethylamine and diisopropylethylamine. The reaction is generally carried out at room temperature to about 60° C. Following the reaction, the product of interest may be isolated in a general manner.

In addition, when the product of interest has a substituted or unsubstituted amino group as group $R^1$, such a compound may be prepared by amidating the product of interest, in which $R^1$ is a hydroxyl group or a $C_{1-6}$-alkoxy group, using amines corresponding to $R^1$, such as methylamine, picolylamine, hydroxylamine and morpholine.

Method (3) Where $R^6$ is a Cyano or $C_{1-6}$-alkoxy-carbonyl Group, Y is an Oxygen Atom, and $R^5$ is a Hydrogen Atom in Formula (I):

Compound (I) may be prepared by reacting a benzaldehyde derivative of formula (VIII):

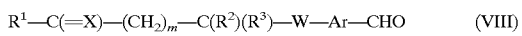

$$R^1-C(=X)-(CH_2)_m-C(R^2)(R^3)-W-Ar-CHO \quad (VIII)$$

wherein

Ar, $R^1$, $R^2$, $R^3$, m and W are as defined above;

with an active methylene compound of formula (IX):

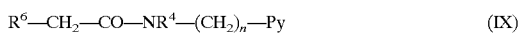

$$R^6-CH_2-CO-NR^4-(CH_2)_n-Py \quad (IX)$$

wherein $R^6$ is a cyano or $C_{1-6}$-alkoxy-carbonyl group; and

Py, $R^4$ and n are as defined above;

through Knoevenagel condensation in the presence of a base catalyst.

Benzaldehyde derivative (VIII) and active methylene compound (IX), which are used as starting materials, are commercially available or may be prepared in a general manner.

This reaction may use an appropriate inert solvent, including organic solvents such as benzene, toluene and ethanol. A base catalyst that can be used in the reaction includes pyridine and piperidine. The reaction may be carried out at 80° C. to 140° C. Following the reaction, the product of interest may be isolated in a general manner.

Method (4) Where Y is a Sulfur Atom in Formula (I):

The compound of interest may be prepared by reacting the compound obtained from the above methods (1) to (3), i.e., an amide derivative in which Y is an oxygen atom in formula (I), with a sulfurizing agent such as Lawesson reagent for conversion into a thione derivative. This reaction may be carried out in an inert solvent, including toluene and xylene, in general, at 110° C. to 140° C. Following the reaction, the product of interest may be isolated in a general manner.

The product may be purified by any procedure commonly used, including column chromatography on silica gel or the like and recrystallization from ethyl acetate, acetone, hexane, methanol, ethanol, chloroform, dimethyl sulfoxide, water or the like. Examples of elution solvents for column chromatography include chloroform, methanol, acetone, hexane, dichloromethane, ethyl acetate, and combinations thereof.

The compound of formula (I) and pharmaceutically acceptable salt thereof (hereinafter, designated "cinnamamide derivative (I)") have inhibitory activities against IL-6, IL-10 and IL-12 production and/or thromboxane $A_2$ synthase. Such a compound may be an effective therapeutic agent for autoimmune diseases (e.g., nephrotic syndrome, immunological rejection in transplantation, rheumatism, allergy), circulatory disorders (e.g., ischemic heart disease, thromboembolic disorder, disorder of cerebral circulation), respiratory diseases (e.g., asthma), diabetes, liver disorders, tumors and the like. In particular, it may be an effective prophylactic or therapeutic agent for nephrotic syndrome.

Cinnamamide derivative (I) will be described with respect to a dose for administration and the formulation.

Cinnamamide derivative (I) can be administered to an animal and a human with or without a conventional pharmaceutical carrier. It may be formulated into any suitable pharmaceutical form as needed, including, but not limited to, oral formulations such as tablets, capsules, granules, fine granules and powders, as well as parenteral formulations such as injections and suppositories.

A daily dose of the oral formulation may vary depending on the age, weight and disease condition of a patient. In order to achieve an expected effect as an oral formulation, however, a suitable daily dose for an adult may generally be 1 mg to 2 g, based on the weight of cinnamamide derivative (I), which may be administered at several times per day.

The oral formulation may be prepared in a general manner using, for example, starch, lactose, sucrose, mannitol, carboxymethylcellulose, corn starch and/or inorganic salts.

In addition to these excipients, such a formulation may optionally contain binders, disintegrators, surfactants, lubricants, enhancers for the fluidity, flavoring agents, colorants, perfumes and the like. Specific examples for each ingredient will be presented below:
Binders: starch, dextrin, powdered acacia, gelatin, hydroxypropyl starch, methylcellulose, carboxymethylcellulose sodium, hydroxypropylcellulose, crystalline cellulose, ethylcellulose, polyvinylpyrrolidone, and Macrogol;
Disintegrators: starch, hydroxypropyl starch, carboxymethylcellulose sodium, carboxymethylcellulose calcium, carboxymethylcellulose, and low-substituted hydroxypropylcellulose;
Surfactants: sodium lauryl sulfate, soybean lecithin, sucrose esters of fatty acid, and Polysorbate 80;
Lubricants: talc, waxes, hydrogenated vegetable oils, sucrose esters of fatty acid, magnesium stearate, calcium stearate, aluminum stearate, and polyethylene glycol; and
Enhancers for the fluidity: light anhydrous silicic acid, dried aluminum hydroxide gel, synthetic aluminum silicate, and magnesium silicate.

In addition, cinnamamide derivative (I) may be administered in suspension, emulsion, syrup or elixir, which may further contain corrigents and/or colorants.

A daily dose of the parenteral formulation may vary depending on the age, weight and disease condition of a patient. In order to achieve an expected effect as a parenteral formulation, however, a suitable daily dose for an adult may generally be 0.01 mg to 600 mg, based on the weight of cinnamamide derivative (I), which may be administered by intravenous injection, intravenous drip infusion, subcutaneous injection or intramuscular injection. Such a parenteral formulation may be prepared in a general manner using as a diluent distilled water for injection, physiological saline, aqueous glucose solution, vegetable oils for injection, sesame oil, peanut oil, soybean oil, corn oil, propylene glycol, polyethylene glycol and the like. The formulation may further contain disinfectants, antiseptics and/or stabilizers, if necessary. In view of the stability, the parenteral formulation may also be prepared by the following steps: freezing in a vial etc., standard lyophillization to remove water, followed by reconstitution of a liquid from the lyophilized product immediately before use. Further, the parenteral formulation may also contain optional additives such as isotonicities, stabilizers, antiseptics and/or soothing agents, if necessary.

Other parenteral formulations may be paints, such as external liquid preparations and ointments, and suppositories for intrarectal administration, which may be prepared in a general manner.

This specification includes part or all of the contents as disclosed in the specification of Japanese Patent Application No. 11-4384, which is a priority document of the present application.

BEST MODE FOR CARRYING OUT THE INVENTION

The present invention will be further described in the following examples, which are provided for illustrative purposes only, and are not intended to limit the scope of the invention.

EXAMPLE 1

Synthesis of Ethyl [4-[(E)-2-[N-(3-Pyridylmethyl)carbamoyl]ethenyl]phenoxy]acetate

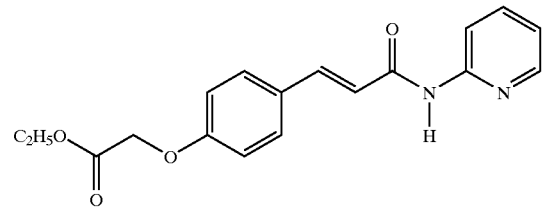

3.74 g of 4-[(2-methoxyethoxy)methoxy]cinnamic acid and 1.68 g of 3-(aminomethyl)pyridine were dissolved in 30 ml dimethylformamide, and stirred with 2.7 ml diethylphosphoryl cyanide and subsequently with 2.5 ml triethylamine on ice, followed by further stirring at room temperature for 1 hour. Saturated aqueous sodium bicarbonate was added to the reaction mixture, which was then extracted with ethyl acetate, washed with water, and dried over magnesium sulfate. The solvent was evaporated under reduced pressure to give a residue, which was then purified via column chromatography on silica gel (chloroform:methanol=50:1) to provide (E)-3-[4-[(2-methoxyethoxy)methoxy]phenyl]-N-(3-pyridylmethyl)-2-propenoic acid amide as a pale yellow oil (4.54 g, 89%).

$^1$H-NMR (CDCl$_3$) δ: 3.36 (3H, s), 3.52–3.57 (2H, m), 3.79–3.83 (2H, m), 4.55 (2H, d, J=5.9 Hz), 5.27 (2H, s), 6.53 (1H, d, J=15.6 Hz), 6.69 (1H, t, J=5.9 Hz), 7.01 (2H, d, J=8.7 Hz), 7.21–7.28 (1H, m), 7.40 (2H, d, J=8.7 Hz), 7.61 (1H, d, J=15.6 Hz), 7.65–7.70 (1H, m), 8.47–8.52 (2H, m).

4.06 g of (E)-3-[4-[(2-methoxyethoxy)methoxy]phenyl]-N-(3-pyridylmethyl)-2-propenoic acid amide was dissolved in 100 ml of 25% HCl/methanol and stirred at room temperature for 1 hour. The solvent was evaporated under reduced pressure to give (E)-3-(4-hydroxyphenyl)-N-(3-pyridylmethyl)-2-propenoic acid amide hydrochloride as a colorless solid, which was then dissolved in 40 ml dimethylformamide and stirred with 10.2 g of potassium carbonate and 2.5 ml of ethyl bromoacetate at room temperature for 2 hours. After addition of ethyl acetate, the reaction mixture was filtered to remove insoluble products. The resulting filtrate was washed with water and dried over magnesium sulfate. The solvent was evaporated under reduced pressure to give a residue, which was then purified via column chromatography on silica gel (chloroform:methanol=50:1), followed by recrystallization, to provide the compound of interest (2.31 g, 58%).

Properties: mp 116–120° C. (ethyl acetate/hexane); $^1$H-NMR (CDCl$_3$) δ: 1.30 (3H, t, J=7.1 Hz), 4.27 (2H, q, J=7.1 Hz), 4.58 (2H, d, J=5.8 Hz), 4.64 (2H, s), 6.16 (1H, t, J=5.8 Hz), 6.31 (1H, d, J=15.6 Hz), 6.89 (2H, d, J=8.8 Hz), 7.24–7.30 (1H, m), 7.44 (2H, d, J=8.8 Hz), 7.63 (1H, d, J=15.6 Hz), 7.67–7.71 (1H, m), 8.52–8.56 (2H, m).

EXAMPLE 2

Synthesis of Ethyl [4-[(E)-2-[N-Methyl-N-(3-pyridylmethyl)carbamoyl]ethenyl]phenoxy]-acetate

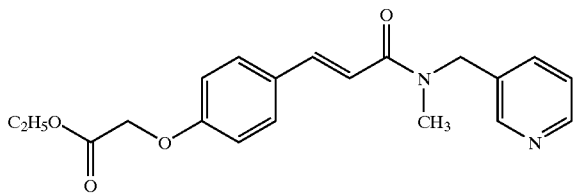

22.87 g of 3-(aminomethyl)pyridine was dissolved in 100 ml dichloromethane and stirred with 50.4 ml ethyl trifluoroacetate and 29.5 ml triethylamine at room temperature for 2 hours. The solvent was evaporated under reduced pressure to give a residue, which was then recrystallized from ethyl acetate to provide N-(3-pyridylmethyl)trifluoroacetic acid amide (40.15 g, 93%).

Properties: mp 102.0–103.5° C. (ethyl acetate); $^1$H-NMR (CDCl$_3$) δ: 4.53 (2H, d, J=6.0 Hz), 7.31 (1H, dd, J=7.3, 4.8 Hz), 7.64–7.70 (1H, m), 7.85–8.15 (1H, br), 8.42 (1H, d, J=2.0 Hz), 8.48 (1H, dd, J=4.8, 1.6 Hz).

4.08 g of N-(3-pyridylmethyl)trifluoroacetic acid amide was dissolved in 40 ml dimethylformamide, and then stirred with 880 mg of 60% sodium hydride on ice for 15 minutes. 1.47 ml methyl iodide was added to the reaction mixture on ice, followed by stirring at room temperature for 4 hours. After addition of water, the reaction mixture was extracted with ethyl acetate, washed with water, and then dried over magnesium sulfate. The solvent was evaporated under reduced pressure to give a residue, which was then purified via column chromatography on silica gel (chloroform:methanol=50:1) to provide N-methyl-N-(3-pyridylmethyl)trifluoroacetic acid amide (3.71 g, 85%) as a pale yellow oil.

$^1$H-NMR (CDCl$_3$) δ: 2.95–3.13 (3H, m), 4.66–4.69 (2H, m), 7.29–7.40 (1H, m), 7.56–7.68 (1H, m), 8.53–8.64 (2H, m).

3.71 g of N-methyl-N-(3-pyridylmethyl)trifluoroacetic acid amide was dissolved in a mixture of 20 ml methanol and 20 ml water, and then stirred with 1.36 g of sodium hydroxide at room temperature for 6 hours. The reaction mixture was made acidic (pH 2) with concentrated hydrochloric acid on ice, and the resulting acidic solution was concentrated under reduced pressure to give a residue. After addition of ethanol, the residue was filtered to remove the precipitated inorganic salts. The filtrate was concentrated under reduced pressure, dried and then recrystallized from methanol/ethanol to give 3-(methylaminomethyl)pyridine dihydrochloride (3.16 g, 95%).

$^1$H-NMR (CD$_3$OD) δ: 2.85 (3H, s), 4.55 (2H, s), 8.18–8.26 (1H, m), 8.86–8.93 (1H, m), 8.97–9.01 (1H, m), 9.17–9.19 (1H, m).

1.03 g of 4-acetoxycinnamic acid and 0.61 g of 3-(methylaminomethyl)pyridine were dissolved in 5 ml dimethylformamide, and then stirred with 0.90 ml diethylphosphoryl cyanide and subsequently with 0.75 ml triethylamine on ice for 2 hours. After addition of water, the reaction mixture was extracted with ethyl acetate, washed with brine, and then dried over magnesium sulfate. The solvent was evaporated under reduced pressure to give a residue, which was then purified via column chromatography on silica gel (dichloromethane:methanol=30:1) to provide 4[(E)-2-[N-methyl-N-(3-pyridylmethyl)carbamoyl]ethenyl]phenyl acetate (1.50 g).

$^1$H-NMR (CDCl$_3$) δ: 2.31 (3H, s), 3.07–3.12 (3H, m), 4.72 (2H, s), 6.77–6.91 (1H, m), 7.09–7.14 (2H, m), 7.28–7.32 (1H, m), 7.46–7.80 (4H, m), 8.55–8.57 (2H, m).

1.50 g of 4-[(E)-2-[N-methyl-N-(3-pyridylmethyl)carbamoyl]ethenyl]phenyl acetate was dissolved in 10 ml methanol, and then stirred with 1 ml of water and 0.36 g of potassium hydroxide at room temperature for 1.5 hours. After the reaction mixture was concentrated under reduced pressure, the residue was neutralized with diluted hydrochloric acid, extracted with ethyl acetate, washed with water, and then dried over magnesium sulfate. The solvent was evaporated under reduced pressure to give a residue, which was then purified via column chromatography on silica gel (dichloromethane:methanol=30:1) to provide (E)-3-(4-hydroxyphenyl)-N-methyl-N-(3-pyridylmethyl)-2-propenoic acid amide (1.00 g).

$^1$H-NMR (DMSO-d$_6$) δ: 2.91–3.13 (3H, m), 4.62–4.85 (2H, m), 6.76–6.81 (2H, m), 6.96–7.12 (1H, m), 7.33–7.68 (5H, m), 8.47–8.50 (2H, m), 9.87 (1H, brs).

1.00 g of (E)-3-(4-hydroxyphenyl)-N-methyl-N-(3-pyridylmethyl)-2-propenoic acid amide was dissolved in 10 ml dimethylformamide, and then stirred with 1.25 g of potassium carbonate and 0.50 ml of ethyl chloroacetate at 40° C. for 1.5 hours. After addition of ethyl acetate, the reaction mixture was washed with water, and then dried over magnesium sulfate. The solvent was evaporated under reduced pressure to give a residue, which was then purified via column chromatography on silica gel (dichloromethane:methanol=50:1), followed by recrystallization, to provide the compound of interest (0.92 g, 52% after 3 steps).

Properties: mp 72–74° C. (dichloromethane/ether); $^1$H-NMR (DMSO-d$_6$, 100° C.) δ: 1.21 (3H, t, J=7.1 Hz), 3.04 (3H, s), 4.18 (2H, q, J=7.1 Hz), 4.69 (2H, s), 4.74 (2H, s), 6.94 (2H, d, J=8.8 Hz), 7.01 (1H, d, J=15.4 Hz), 7.28–7.36 (1H, m), 7.48 (1H, d, J=15.4 Hz), 7.58 (2H, d, J=8.8 Hz), 7.60–7.67 (1H, m), 8.43–8.50 (2H, m).

EXAMPLES 3 TO 35

The following compounds were obtained in the same manner as described in Example 1 or 2.

EXAMPLE 3

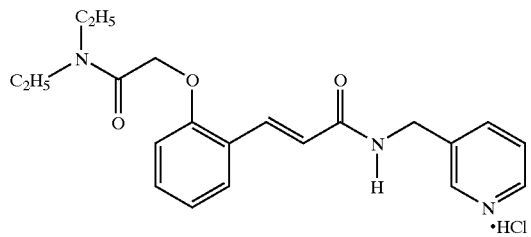

Properties: amorphous; $^1$H-NMR (DMSO-d$_6$) δ: 1.0 (3H, t, J=7 Hz), 1.1 (3H, t, J=7 Hz), 3.1–3.4 (4H, m), 4.5 (2H, d, J=6 Hz), 4.9 (2H, s), 6.7 (1H, d, J=16 Hz), 6.9–7.3 (3H, m), 7.5 (1H, d, J=8 Hz), 7.8 (1H, d, J=16 Hz), 8.0 (1H, dd, J=8,6 Hz), 8.4 (1H, d, J=8 Hz), 8.8 (2H, m), 8.9 (1H, t, J=6 Hz).

EXAMPLE 4

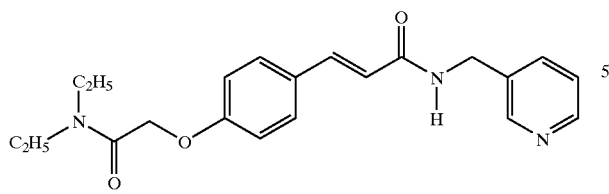

Properties: mp 123–127° C. (ethyl acetate/hexane); $^1$H-NMR (DMSO-d$_6$) δ: 1.0 (3H, t, J=7 Hz), 1.2 (3H, t, J=7 Hz), 3.2–3.4 (4H, m), 4.4 (2H, d, J=6 Hz), 4.8 (2H, s), 6.5 (1H, d, J=16 Hz), 6.9 (2H, d, J=9 Hz), 7.3–7.5 (2H, m), 7.5 (2H, d, J=9 Hz), 7.7 (1H, m), 8.5 (2H, m), 8.6 (1H, t, J=6 Hz).

EXAMPLE 5

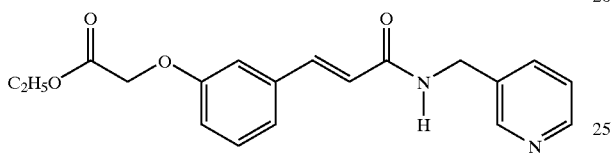

Properties: mp 109.5° C. (ethyl acetate); $^1$H-NMR (CDCl$_3$) δ: 1.30 (3H, t, J=7.2 Hz), 4.27 (2H, q, J=7.2 Hz), 4.59 (2H, d, J=5.9 Hz), 4.63 (2H, s), 6.27 (1H, brt, J=5.9 Hz), 6.40 (1H, d, J=15.7 Hz), 6.74–6.91 (1H, m), 6.91–7.04 (1H m), 7.13 (1H, d, J=7.7 Hz), 7.24–7.33 (2H, m), 7.62 (1H, d, J=15.7 Hz), 7.66–7.73 (1H, m), 8.51–8.54 (1H, m), 8.56–8.57 (1H, m).

EXAMPLE 6

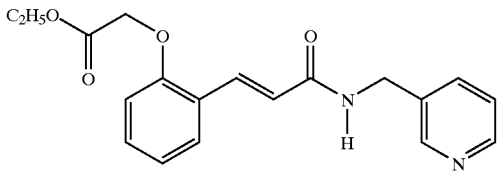

Properties: mp 92.7° C. (ethyl acetate); $^1$H-NMR (CDCl$_3$) δ: 1.29 (3H, t, J=7.1 Hz), 4.26 (2H, q, J=7.1 Hz), 4.60 (2H, d, J=6.0 Hz), 4.68 (2H, s), 6.16–6.23 (1H, br), 6.79 (1H, d, J=8.3 Hz), 6.90 (1H, d, J=15.8 Hz), 6.96–7.04 (1H, m), 7.23–7.34 (2H, m), 7.44–7.49 (1H, m), 7.67–7.74 (1H, m), 7.86 (1H, d, J=15.8 Hz), 8.51–8.54 (1H, m), 8.57–8.58 (1H, m).

EXAMPLE 7

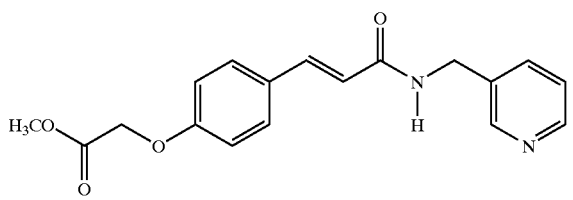

Properties: mp 138.7° C. (methanol); $^1$H-NMR (CDCl$_3$) δ: 3.82 (3H, s), 4.60 (2H, d, J=6.0 Hz), 4.66 (2H, s), 5.94–6.10 (1H, br), 6.30 (1H, d, J=15.6 Hz), 6.90 (2H, d, J=8.8 Hz), 7.24–7.32 (1H, m), 7.46 (2H, d, J=8.8 Hz), 7.64 (1H, d, J=15.6 Hz), 7.66–7.72 (1H, m), 8.52–8.59 (2H, m).

EXAMPLE 8

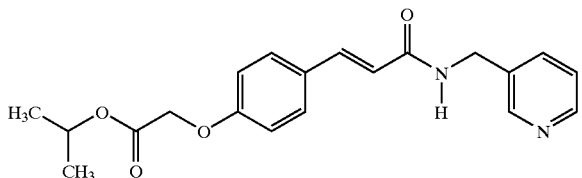

Properties: mp 139.9° C. (isopropanol); $^1$H-NMR (CDCl$_3$) δ: 1.27 (6H, d, J=6.3 Hz), 4.58 (2H, d, J=7.6 Hz), 4.60 (2H, s), 5.14 (1H, seven, J=6.3 Hz), 6.18 (1H, brt), 6.31 (1H, d, J=15.7 Hz), 6.88 (2H, d, J=8.8 Hz), 7.23–7.30 (1H, m), 7.43 (2H, d, J=8.8 Hz), 7.63 (1H, d, J=15.7 Hz), 7.65–7.72 (1H, m), 8.50–8.57 (2H, m).

EXAMPLE 9

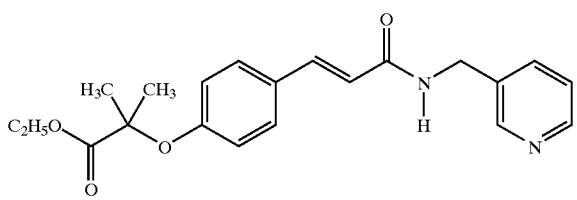

Properties: mp 103.2° C. (diethyl ether/dichloromethane); $^1$H-NMR (CDCl$_3$) δ: 1.23 (3H, t, J=7.1 Hz), 1.62 (6H, s), 4.23 (2H, q, J=7.1 Hz), 4.57 (2H, d, J=6.0 Hz), 6.17–6.24 (1H, br), 6.30 (1H, d, J=15.6 Hz), 6.79 (2H, d, J=8.7 Hz), 7.22–7.29 (1H, m), 7.38 (2H, d, J=8.7 Hz), 7.61 (1H, d, J=15.6 Hz), 7.64–7.71 (1H, m), 8.50–8.56 (2H, m).

EXAMPLE 10

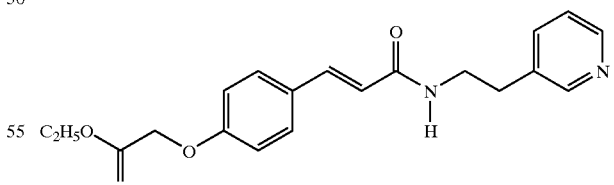

Properties: mp 121.6° C. (ethyl acetate); $^1$H-NMR (CDCl$_3$) δ: 1.30 (3H, t, J=7.1 Hz), 2.90 (2H, t, J=6.9 Hz), 3.59–3.70 (2H, m), 4.27 (2H, q, J=7.1 Hz), 4.64 (2H, s), 5.79 (1H, brt), 6.22 (1H, d, J=15.5 Hz), 6.88 (2H, d, J=8.8 Hz), 7.21–7.28 (1H, m), 7.43 (2H, d, J=8.8 Hz), 7.54–7.59 (1H, m), 7.57 (1H, d, J=15.5 Hz), 8.46–8.50 (2H, m).

EXAMPLE 11

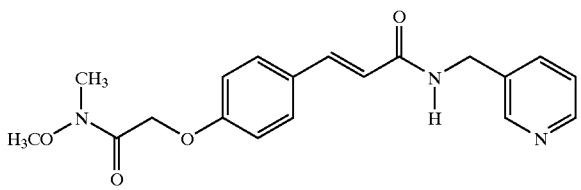

Properties: mp 153.3° C. (methanol); $^1$H-NMR (CDCl$_3$) δ: 3.23 (3H, s), 3.77 (3H, s), 4.57 (2H, d, J=6.0 Hz), 4.83 (2H, s), 6.25–6.31 (1H, m), 6.28 (1H, d, J=15.6 Hz), 6.90 (2H, d, J=8.8 Hz), 7.23–7.30 (1H, m), 7.41 (2H, d, J=8.8 Hz), 7.61 (1H, d, J=15.6 Hz), 7.65–7.72 (1H, m), 8.50–8.56 (2H, m).

EXAMPLE 12

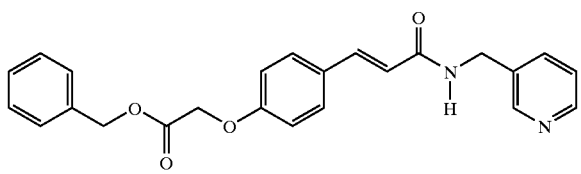

Properties: mp 115.2° C. (dichloromethane/hexane); $^1$H-NMR (CDCl$_3$) δ: 4.58 (2H, d, J=6.0 Hz), 4.68 (2H, s), 5.24 (2H, s), 6.08 (1H, brt), 6.29 (1H, d, J=15.6 Hz), 6.87 (2H, d, J=8.8 Hz), 7.23–7.39 (6H, m), 7.42 (2H, d, J=8.8 Hz), 7.63 (1H, d, J=15.6 Hz), 7.65–7.72 (1H, m), 8.51–8.57 (2H, m).

EXAMPLE 13

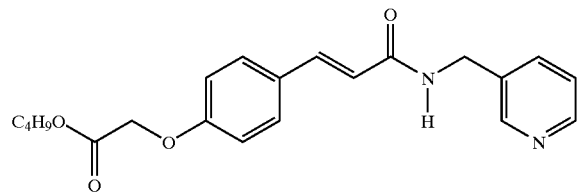

Properties: mp 81° C. (dichloromethane/hexane); $^1$H-NMR (CDCl$_3$) δ: 0.91 (3H, t, J=7.3 Hz), 1.25–1.44 (2H, m), 1.56–1.71 (2H, m), 4.21 (2H, t, J=6.6 Hz), 4.58 (2H, d, J=5.9 Hz), 4.64 (2H, s), 6.15 (1H, brt, J=5.9 Hz), 6.30 (1H, d, J=15.6 Hz), 6.88 (2H, d, J=8.8 Hz), 7.23–7.30 (1H, m), 7.44 (2H, d, J=8.8 Hz), 7.63 (1H, t, J=15.6 Hz), 7.65–7.72 (1H, m), 8.51–8.56 (2H, m).

EXAMPLE 14

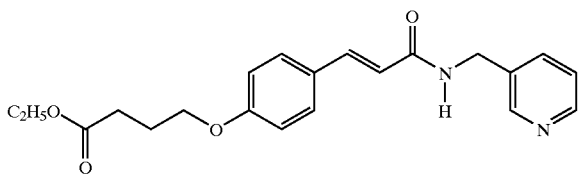

Properties: mp 123.1° C. (dichloromethane); $^1$H-NMR (CDCl$_3$) δ: 1.26 (3H, t, J=7.1 Hz), 2.04–2.19 (2H, m), 2.51 (2H, t, J=7.2 Hz), 4.03 (2H, t, J=6.1 Hz), 4.15 (2H, q, J=7.1 Hz), 4.59 (2H, d, J=6.0 Hz), 5.99 (1H, brt), 6.28 (1H, d, J=15.6 Hz), 6.87 (2H, d, J=8.7 Hz), 7.23–7.31 (1H, m), 7.43 (2H, d, J=8.7 Hz), 7.63 (1H, d, J=15.6 Hz), 7.66–7.80 (1H, m), 8.52–8.57 (2H, m).

EXAMPLE 15

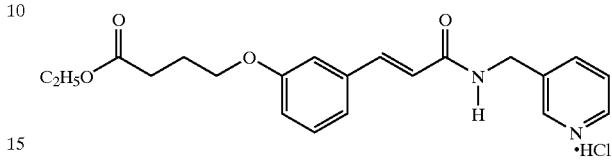

Properties: mp 140.2° C. (ethanol/diethyl ether); $^1$H-NMR (DMSO-d$_6$) δ: 1.18 (3H, t, J=7.1 Hz), 1.90–2.05 (2H, m), 2.42–2.50 (2H, m), 3.99–4.13 (4H, m), 4.58 (2H, d, J=5.9 Hz), 6.73 (1H, d, J=15.8 Hz), 6.92–6.98 (1H, m), 7.12–7.18 (2H, m), 7.33 (1H, t, J=7.8 Hz), 7.45 (1H, d, J=15.8 Hz), 7.93–8.01 (1H, m), 8.38–8.43 (1H, m), 8.77–8.83 (2H, m), 8.96 (1H, brt, J=5.9 Hz).

EXAMPLE 16

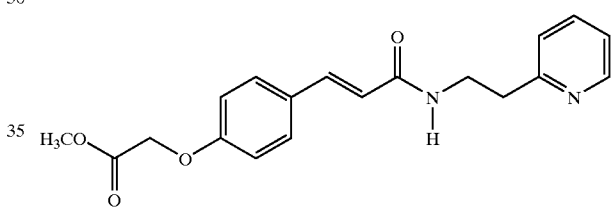

Properties: mp 117.2° C. (ethyl acetate); $^1$H-NMR (CDCl$_3$) δ: 3.05 (2H, t, J=6.2 Hz), 3.75–3.85 (2H, m), 3.81 (3H, s), 4.65 (2H, s), 6.26 (1H, d, J=15.5 Hz), 6.55–6.74 (1H, br), 6.88 (2H, d, J=8.8 Hz), 7.12–7.22 (2H, m), 7.46 (2H, d, J=8.8 Hz), 7.55 (1H, d, J=15.5 Hz), 7.62–7.68 (1H, m), 8.54–8.57 (1H, m).

EXAMPLE 17

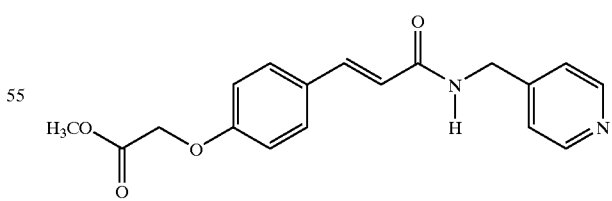

Properties mp 143.3° C. (ethyl acetate); $^1$H-NMR (CDCl$_3$) δ: 3.81 (3H, s), 4.58 (2H, d, J=6.0 Hz), 4.66 (2H, s), 6.21 (1H, brt, J=6.0 Hz), 6.35 (1H, d, J=15.6 Hz), 6.89 (2H, d, J=8.8 Hz), 7.20–7.24 (2H, m), 7.45 (2H, d, J=8.8 Hz), 7.64 (1H, d, J=15.5 Hz), 8.53–8.57 (2H, m).

EXAMPLE 18

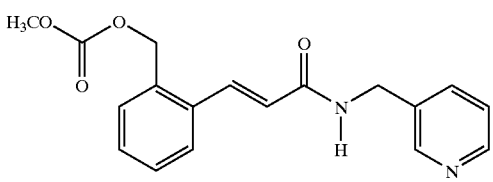

Properties: mp 113–116° C. (ethyl acetate); ¹H-NMR (CDCl₃) δ: 3.80 (3H, s), 4.60 (2H, d, J=6.0 Hz), 4.70 (2H, s), 6.21 (1H, brt), 6.78 (1H, d, J=8.1 Hz), 6.88 (1H, d, J=15.8 Hz), 7.00 (1H, dd, J=7.5, 6.8 Hz), 7.23–7.34 (2H, m), 7.44–7.50 (1H, m), 7.67–7.74 (1H, m), 7.87 (1H, d, J=15.8 Hz), 8.52 (1H, dd, J=4.8, 1.6 Hz), 8.58 (1H, d, J=2.0 Hz).

EXAMPLE 19

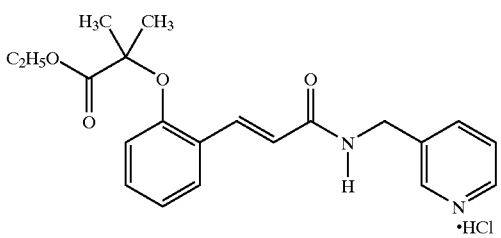

Properties: oil; ¹H-NMR (DMSO-d₆) δ: 1.16 (3H, t, J=7.1 Hz), 1.58 (6H, s), 4.18 (2H, q, J=7.1 Hz), 4.60 (2H, d, J=5.8 Hz), 6.70–6.81 (2H, m), 7.00–7.07 (1H, m), 7.27–7.35 (1H, m), 7.58–7.62 (1H, m), 7.76 (1H, d, J=16.0 Hz), 8.02 (1H, dd, J=8.0, 5.6 Hz), 8.48 (1H, brd, J=8.0 Hz), 8.83 (1H, brd, J=5.6 Hz), 8.87 (1H, brs), 9.14 (1H, brt, J=5.8 Hz).

EXAMPLE 20

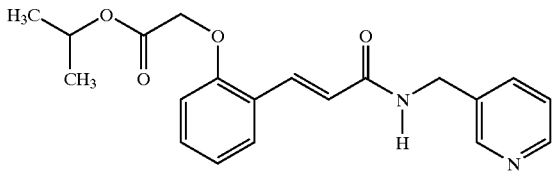

Properties: mp 150–151.7° C. (ethyl acetate); ¹H-NMR (CDCl₃) δ: 1.26 (6H, d, J=6.3 Hz), 4.59 (2H, d, J=6.0 Hz), 4.64 (2H, s), 5.12 (1H, sept, J=6.3 Hz), 6.36 (1H, m), 6.77 (1H, d, J=8.2 Hz), 6.90 (1H, d, J=15.8 Hz), 7.02 (1H, m), 7.22–7.33 (2H, m), 7.45 (1H, dd, J=7.6, 1.5 Hz), 7.67–7.72 (1H, m), 7.87 (1H, d, J=15.8 Hz), 8.51 (1H, dd, J=4.8, 1.5 Hz), 8.56 (1H, d, J=1.8 Hz).

EXAMPLE 21

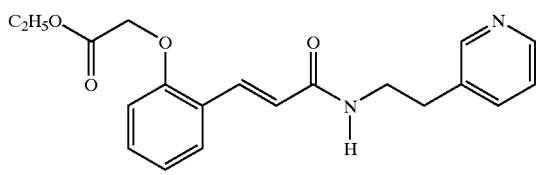

Properties: mp 98.0–99.0° C. (ethyl acetate/hexane); ¹H-NMR (CDCl₃) δ: 1.30 (3H, t, J=7.1 Hz), 2.91 (2H, t, J=7.0 Hz), 3.60–3.70 (2H, m), 4.27 (2H, q, J=7.1 Hz), 4.68 (2H, s), 5.90–5.96 (1H, m), 6.76–6.80 (1H, m), 6.80 (1H, d, J=15.8 Hz), 6.96–7.03 (1H, m), 7.22–7.33 (2H, m), 7.44–7.48 (1H, m), 7.55–7.61 (1H, m), 7.82 (1H, d, J=15.8 Hz), 8.47–8.49 (2H, m).

EXAMPLE 22

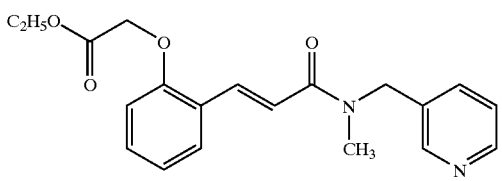

Properties: oil; ¹H-NMR (DMSO-d₆, 100° C.) δ: 1.16–1.24 (3H, m), 2.81–2.96 (3H, m), 4.11–4.23 (2H, m), 4.52–4.70 (2H, m), 4.72–4.81 (2H, m), 6.90–7.03 (2H, m), 7.25–7.36 (3H, m), 7.61–7.66 (2H, m), 7.79 (1H, d, J=15.6 Hz), 845–8.51 (2H, m).

EXAMPLE 23

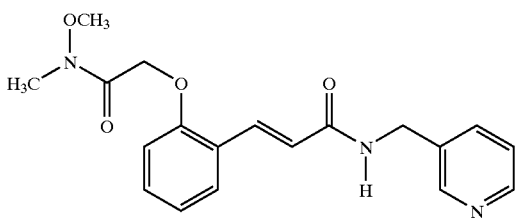

Properties: mp 146.8–147.8° C. (ethyl acetate/chloroform); ¹H-NMR (CDCl₃) δ: 3.21 (3H, s), 3.74 (3H, s), 4.55 (2H, d, J=6.0 Hz), 4.85 (2H, s), 6.65–6.71 (1H, m), 6.83 (1H, d, J=8.2 Hz), 6.91–6.99 (1H, m), 7.00 (1H, d, J=15.8 Hz), 7.20–7.31 (2H, m), 7.41 (1H, dd, J=7.6, 1.6 Hz), 7.67–7.71 (1H, m), 7.84 (1H, d, J=15.8Hz), 8.47–8.54 (2H, m).

EXAMPLE 24

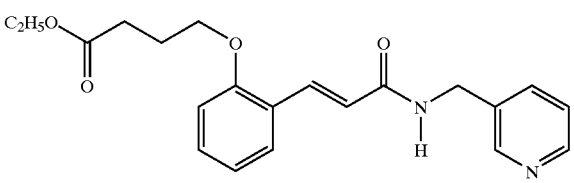

Properties: mp 106.1–108.0° C. (ethyl acetate); ¹H-NMR (CDCl₃) δ: 1.17 (3H, t, J=7.1 Hz), 2.13–2.26 (2H, m), 2.50–2.57 (2H, m), 3.96–4.10 (4H, m), 4.60 (2H, d, J=6.0 Hz), 6.73 (1H, d, J=15.9 Hz), 6.80–6.98 (3H, m), 7.23–7.33 (2H, m), 7.41–7.47 (1H, m), 7.69–7.74 (1H, m), 7.79 (1H, d, J=15.9 Hz), 8.51 (1H, dd, J=4.8, 1.4 Hz), 8.59 (1H, d, J=1.8 Hz).

EXAMPLE 25

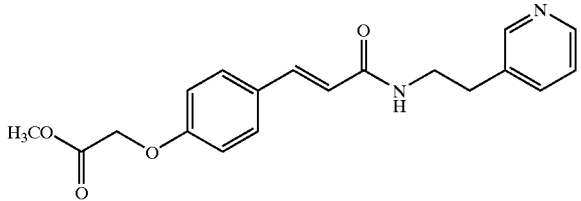

Properties: mp 137–140° C. (ethyl acetate/hexane); $^1$H-NMR (CDCl$_3$) δ: 2.91 (2H, t, J=6.9 Hz), 3.60–3.70 (2H, m), 3.81 (3H, s), 4.66 (2H, s), 5.67–5.73 (1H, m), 6.21 (1H, d, J=15.5 Hz), 6.88 (2H, d, J=8.8 Hz), 7.22–7.28 (1H, m), 7.43 (2H, d, J=8.8 Hz), 7.54–7.58 (1H, m), 7.58 (1H, d, J=15.5 Hz), 8.48 (2H, brs).

EXAMPLE 26

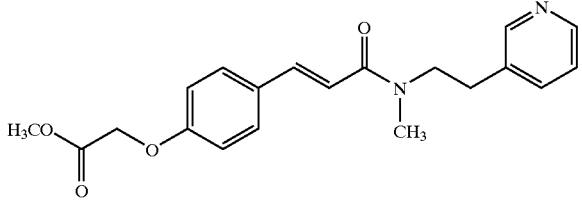

Properties: mp 106.1–107.5° C. (ethyl acetate/hexane); $^1$H-NMR (DMSO-d$_6$, 100° C.) δ: 2.84–2.92 (2H, m), 3.00 (3H, s), 3.66–3.73 (2H, m), 3.71 (3H, s), 4.77 (2H, s), 6.82 (1H, d, J=15.4 Hz), 6.94 (2H, d, J=8.7 Hz), 7.25 (1H, dd, J=7.7, 4.7 Hz), 7.35 (1H, d, J=15.4 Hz), 7.53 (2H, d, J=8.7 Hz), 7.60–7.66 (1H, m), 8.38 (1H, dd, J=4.7, 1.3 Hz), 8.46 (1H, d, J=1.8 Hz).

EXAMPLE 27

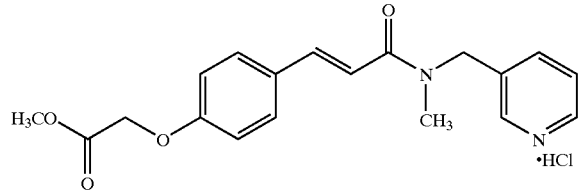

Properties: solid; $^1$H-NMR (DMSO-d$_6$, 100° C.) δ: 3.10 (3H, s), 3.71 (3H, s), 4.66–4.78 (4H, m), 6.91–7.05 (3H, m), 7.49 (1H, d, J=15.4 Hz), 7.58 (2H, d, J=8.8 Hz), 7.73 (1H, dd, J=7.9, 5.4 Hz), 8.11 (1H, d, J=7.9 Hz), 8.63–8.66 (2H, m).

EXAMPLE 28

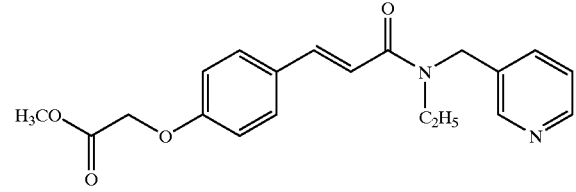

Properties: mp 99.3–100.3° C. (ethyl acetate/hexane); $^1$H-NMR (DMSO-d$_6$, 100° C.) δ: 1.11 (3H, t, J=7.1 Hz), 3.49 (2H, q, J=7.1 Hz), 3.71 (3H, s), 4.68 (2H, s), 4.77 (2H, s), 6.92–7.00 (3H, m), 7.31 (1H, dd, J=7.9, 4.8 Hz), 7.46–7.59 (3H, m), 7.62–7.69 (1H, m), 8.45 (1H, dd, J=4.8, 1.4 Hz), 8.51 (1H, d, J=1.9 Hz).

EXAMPLE 29

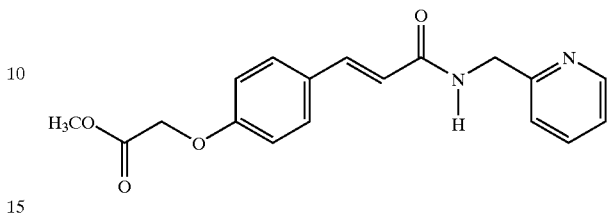

Properties: mp 137–139° C. (ethyl acetate); $^1$H-NMR (CDCl$_3$) δ: 3.81 (3H, s), 4.66 (2H, s), 4.70 (2H, d, J=5.0 Hz), 6.42 (1H, d, J=15.6 Hz), 6.89 (2H, d, J=8.8 Hz), 7.00 (1H, brt), 7.18–7.25 (1H, m), 7.27–7.34 (1H, m), 7.46 (2H, d, J=8.8 Hz), 7.62 (1H, d, J=15.6 Hz), 7.63–7.73 (1H, m), 8.54–8.57 (2H, m).

EXAMPLE 30

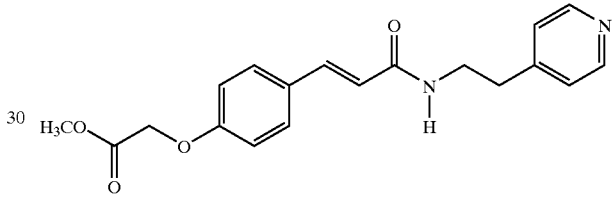

Properties: mp 162–163° C. (ethyl acetate); $^1$H-NMR (CDCl$_3$) δ: 2.90 (2H, t, J=6.9 Hz), 3.61–3.72 (2H, m), 4.66 (2H, s), 3.81 (3H, s), 5.94 (1H, brt), 6.24 (1H, d, J=15.6 Hz), 6.88 (2H, d, J=8.8 Hz), 7.15 (2H, d, J=6.0 Hz), 7.43 (2H, d, J=8.8 Hz), 7.58 (1H, d, J=15.6 Hz), 8.50 (2H, d, J=6.0 Hz).

EXAMPLE 31

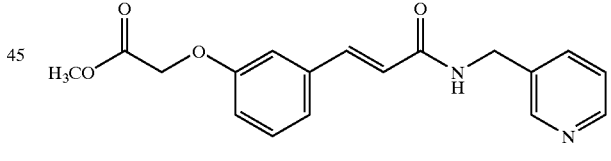

Properties: mp 127° C. (dichloromethane/hexane); $^1$H-NMR (CDCl$_3$) δ: 3.81 (3H, s), 4.60 (2H, d, J=6.0 Hz), 4.65 (2H, s), 6.08 (1H, m), 6.39 (1H, d, J=15.6 Hz), 6.90 (1H, m), 7.04 (1H, m), 7.14 (1H, m), 7.29–7.34 (2H, m), 7.64 (1H, d, J=15.6 Hz), 7.71 (1H, m), 8.53–8.59 (2H, m).

EXAMPLE 32

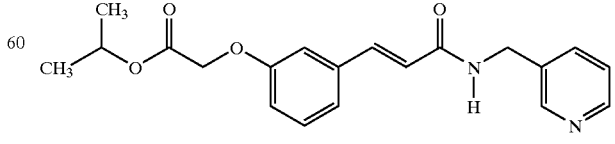

Properties: mp 104° C. (ethyl acetate/hexane); $^1$H-NMR (DMSO-d$_6$) δ: 1.21 (6H, d, J=6.3 Hz), 4.43 (2H, d, J=5.9

Hz), 4.78 (2H, s), 4.99 (1H, m), 6.67 (1H, d, J=15.8 Hz), 6.94 (1H, m), 7.12–7.20 (2H, m), 7.30–7.40 (2H, m), 7.44 (1H, d, J=15.8 Hz), 7.70 (1H, m), 8.45–8.53 (2H, m), 8.69 (1H, m).

EXAMPLE 33

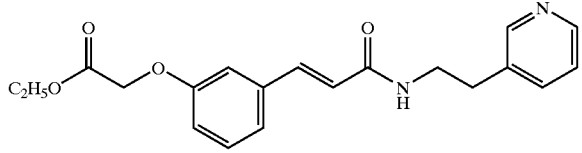

Properties: mp 93–94° C. (dichloromethane/hexane); $^1$H-NMR (DMSO-d$_6$) δ: 1.21 (3H, t, J=7.1 Hz), 2.81 (2H, t, J=7.0 Hz), 3.45 (2H, m), 4.17 (2H, q, J=7.1 Hz), 4.82 (2H, s), 6.59 (1H, d, J=15.8 Hz), 6.94 (1H, m), 7.11–7.18 (2H, m), 7.29–7.41 (3H, m), 7.67 (1H, m), 8.20 (1H, t, J=5.7 Hz), 8.41–8.46 (2H, m).

EXAMPLE 34

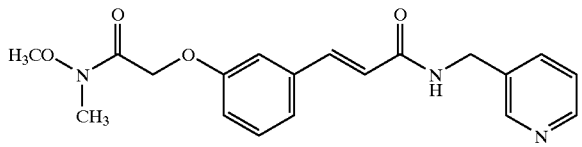

Properties: amorphous; $^1$H-NMR (CDCl$_3$) δ: 3.23 (3H, s), 3.76 (3H, s), 4.57 (2H, d, J=5.9 Hz), 4.82 (2H, s), 6.39 (1H, d, J=15.6 Hz), 6.57 (1H, t, J=5.9 Hz), 6.91 (1H, m), 7.04–7.10 (2H, m), 7.22–7.29 (2H, m), 7.59 (1H, d, J=15.6 Hz), 7.68 (1H, m), 8.50–8.56 (2H, m).

EXAMPLE 35

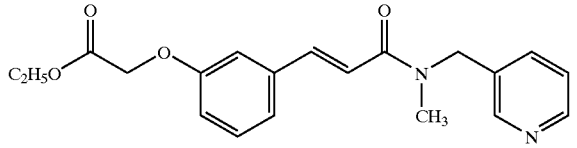

Properties: oil; $^1$H-NMR (DMSO-d$_6$, 100° C.) δ: 1.21 (3H, t, J=7.1 Hz), 3.05 (3H, s), 4.18 (2H, q, J=7.1 Hz), 4.70 (2H, s), 4.75 (2H, s), 6.93 (1H, m), 7.14 (1H, d, J=15.5 Hz), 7.22–7.36 (4H, m), 7.48 (1H, d, J=15.5 Hz), 7.64 (1H, m), 8.45–8.51 (2H, m).

EXAMPLES 36 AND 37

The following compounds were obtained by acid hydrolysis of the compounds from Examples 7 and 18.

EXAMPLE 36

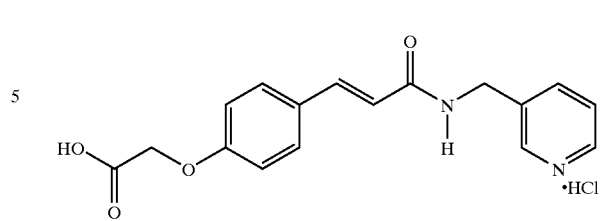

Properties: amorphous; $^1$H-NMR (DMSO-d$_6$) δ: 4.57 (2H, d, J=5.7 Hz), 4.73 (2H, s), 6.59 (1H, d, J=15.8 Hz), 6.96 (2H, d, J=8.7 Hz), 7.44 (1H, d, J=15.8 Hz), 7.53 (2H, d, J=8.7 Hz), 7.99 (1H, dd, J=8.0, 5.6 Hz), 8.42 (1H, d, J=8.0 Hz), 8.79–8.83 (2H, m), 8.92 (1H, t, J=5.7 Hz).

EXAMPLE 37

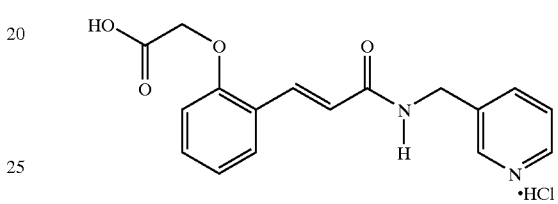

Properties: mp 172–176° C. (water/acetone); $^1$H-NMR (DMSO-d$_6$) δ: 4.57 (2H, d, J=5.8 Hz), 4.81 (2H, s), 6.78 (1H, d, J=16.0 Hz), 6.94–7.05 (2H, m), 7.30–7.39 (1H, m), 7.57 (1H, dd, J=7.7, 1.4 Hz), 7.81 (1H, d, J=16.0 Hz), 7.95 (1H, dd, J=8.0, 5.5 Hz), 8.39 (1H, brd, J=8.0 Hz), 8.79 (1H, brd, J=5.5 Hz), 8.82 (1H, brs), 9.02 (1H, brt, J=5.8 Hz).

EXAMPLE 38

Synthesis of (E)-3-[4-[(Methylcarbamoyl)methoxy]phenyl]-N-(3-pyridylmethyl)-2-propenoic Acid Amide

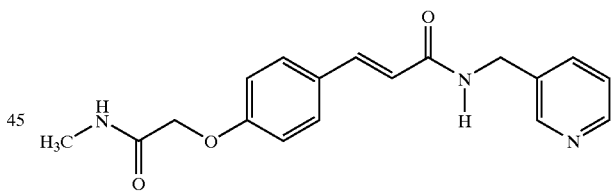

0.41 g (1.2 mmol) of methyl [4-[(E)-2-[N-(3-pyridylmethyl)carbamoyl]ethenyl]phenoxy]acetate from Example 7 was dissolved in 12 ml methanol, and then stirred with 1.0 ml of 40% methylamine solution in methanol at room temperature for 14 hours. The reaction mixture was concentrated under reduced pressure to give a residue, which was then recrystallized to provide the compound of interest (0.31 g, 78%).

Properties: mp 171–172° C. (ethyl acetate/methanol); $^1$H-NMR (DMSO-d$_6$) δ: 2.65 (3H, d, J=4.5 Hz), 4.41 (2H, d, J=5.7 Hz), 4.50 (2H, s), 6.54 (1H, d, J=15.8 Hz), 6.99 (2H, d, J=8.5 Hz), 7.33–7.39 (1H, m), 7.43 (1H, d, J=15.8 Hz), 7.53 (2H, d, J=8.5 Hz), 7.69 (1H, d, J=7.8 Hz), 8.05 (1H, br), 8.46 (1H, d, J=4.7 Hz), 8.52 (1H, s), 8.62 (1H, t, J=5.7 Hz).

EXAMPLES 39 TO 62

The following compounds were obtained in the same manner as describe in Example 36.

EXAMPLE 39

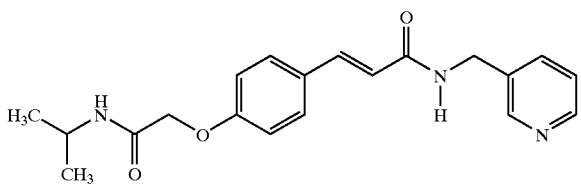

Properties: mp 168–169° C. (ethyl acetate/methanol); $^1$H-NMR (DMSO-d$_6$) δ: 1.09 (6H, d, J=6.6 Hz), 3.82–4.05 (1H, m), 4.42 (2H, d, J=5.9 Hz), 4.48 (2H, s), 6.54 (1H, d, J=15.8 Hz), 6.98 (2H, d, J=8.7 Hz), 7.33–7.37 (1H, m), 7.43 (1H, d, J=15.8 Hz), 7.53 (2H, d, J=8.7 Hz), 7.66–7.72 (1H, m), 7.90–7.94 (1H, m), 8.46 (1H, dd, J=4.8, 1.6 Hz), 8.52 (1H, d, J=1.8 Hz), 8.61 (1H, t, J=5.9 Hz).

EXAMPLE 40

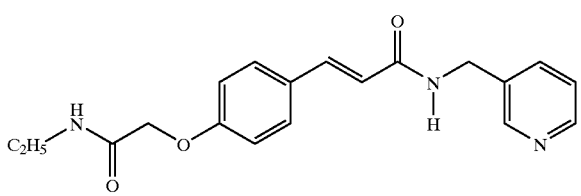

Properties: mp 151–153° C. (ethyl acetate/methanol); $^1$H-NMR (DMSO-d$_6$) δ: 1.04 (3H, t, J=7.2 Hz), 3.09–3.22 (2H, m), 4.42 (2H, d, J=5.8 Hz), 4.49 (2H, s), 6.54 (1H, d, J=15.8 Hz), 6.99 (2H, d, J=8.7 Hz), 7.33–7.39 (1H, m), 7.43 (1H, d, J=15.8 Hz), 7.53 (2H, d, J=8.7 Hz), 7.69 (1H, d, J=7.9 Hz), 8.13 (1H, br), 8.46 (1H, d, J=4.1 Hz), 8.52 (1H, s), 8.63 (1H, t, J=5.8 Hz).

EXAMPLE 41

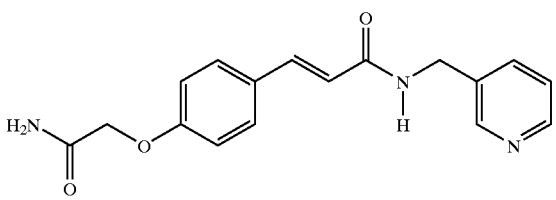

Properties: solid; $^1$H-NMR (DMSO-d$_6$) δ: 4.41 (2H, d, J=5.9 Hz), 4.47 (2H, s), 6.54 (1H, d, J=15.6 Hz), 6.98 (2H, d, J=8.8 Hz), 7.33–7.56 (3H, m), 7.43 (1H, d, J=15.6 Hz), 7.53 (2H, d, J=8.8 Hz), 7.66–7.73 (1H, m), 8.44–8.49 (1H, m), 8.51–8.53 (1H, m), 8.62 (1H, brt, J=5.9 Hz).

EXAMPLE 42

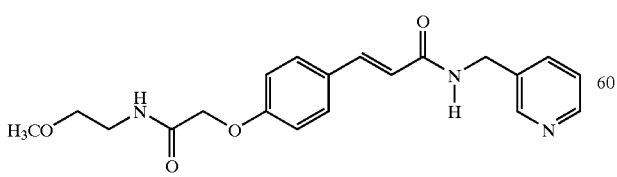

Properties: mp 150.7° C. (ethanol); $^1$H-NMR (CDCl$_3$) δ: 3.34 (3H, s), 3.44–3.59 (4H, m), 4.51 (2H, s), 4.59 (2H, d, J=6.0 Hz), 6.16 (1H, brt), 6.33 (1H, d, J=15.5 Hz), 6.87–6.94 (1H, br), 6.92 (2H, d, J=8.8 Hz), 7.24–7.31 (1H, m), 7.47 (2H, d, J=8.8 Hz), 7.64 (1H, d, J=15.5 Hz), 7.66–7.73 (1H, m), 8.51–8.58 (2H, m).

EXAMPLE 43

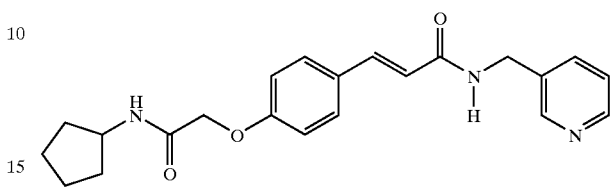

Properties: solid; $^1$H-NMR (CDCl$_3$) δ: 1.37–1.67 (6H, m), 1.94–2.10 (2H, m), 4.20–4.38 (1H, m), 4.47 (2H, s), 4.60 (2H, d, J=5.9 Hz), 6.09 (1H, brt J=5.9 Hz), 6.33 (1H, d, J=15.5 Hz), 6.36–6.45 (1H, br), 6.91 (2H, d, J=8.8 Hz), 7.24–7.31 (1H, m), 7.47 (2H, d, J=8.8 Hz), 7.64 (1H, d, J=15.5 Hz), 7.67–7.73 (1H, m), 8.52–8.59 (2H, m).

EXAMPLE 44

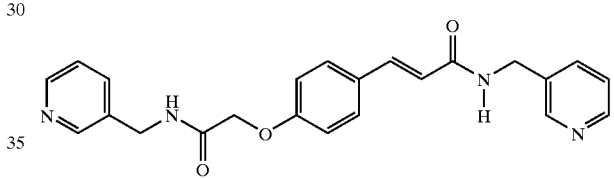

Properties: solid; $^1$H-NMR (DMSO-d$_6$) δ: 4.37 (2H, d, J=6.1 Hz), 4.42 (2H, d, J=5.9 Hz), 4.61 (2H, s), 6.54 (1H, d, J=15.6 Hz), 7.00 (2H, d, J=8.7 Hz), 7.29–7.38 (2H, m), 7.43 (1H, d, J=15.6 Hz), 7.53 (2H, d, J=8.7 Hz), 7.61–7.73 (2H, m), 8.43–8.53 (4H, m), 8.62 (1H, brt, J=5.9 Hz), 8.75 (1H, brt, J=6.1 Hz).

EXAMPLE 45

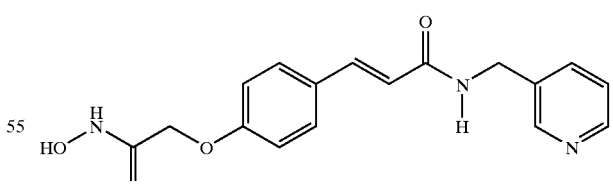

Properties: solid; $^1$H-NMR (DMSO-d$_6$) δ: 4.41 (2H, d, J=5.8 Hz), 4.50 (2H, s), 6.53 (1H, d, J=15.6 Hz), 6.98 (2H, d, J=8.6 Hz), 7.32–7.38 (1H, m), 7.43 (1H, d, J=15.6 Hz), 7.52 (2H, d, J=8.6 Hz), 7.67–7.71 (1H, m), 8.44–8.48 (1H, m), 8.51–8.53 (1H, m), 8.60 (1H, brt, J=5.8 Hz), 8.99 (1H, s), 10.85 (1H, s).

EXAMPLE 46

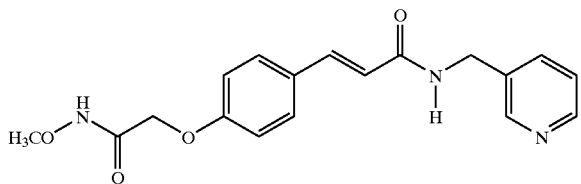

Properties: mp 144.2° C. (acetone); ¹H-NMR (CDCl₃) δ: 3.84 (3H, s), 4.59 (2H, d, J=5.6 Hz), 4.59 (2H, s), 6.04 (1H, brt, J=5.6 Hz), 6.32 (1H, d, J=15.7 Hz), 6.89 (2H, d, J=8.8 Hz), 7.24–7.31 (1H, m), 7.47 (2H, d, J=8.8 Hz), 7.63 (1H, d, J=15.7 Hz), 7.66–7.72 (1H, m), 8.52–8.58 (2H, m), 9.11 (1H, brs).

EXAMPLE 47

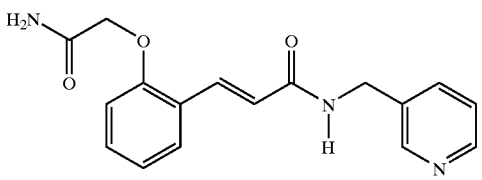

Properties: mp 206–209° C. (water/methanol); ¹H-NMR (DMSO-d₆) δ: 4.43 (2H, d, J=5.8 Hz), 4.56 (2H, s), 6.67 (1H, d, J=16.0 Hz), 6.91 (1H, d, J=8.2 Hz), 7.01 (1H, t, J=7.4 Hz), 7.30–7.58 (5H, m), 7.70 (1H, brd, J=7.9 Hz), 7.82 (1H, d, J=16.0 Hz), 8.47 (1H, d, J=4.0 Hz), 8.53 (1H, br s), 8.68 (1H, t, J=5.8 Hz).

EXAMPLE 48

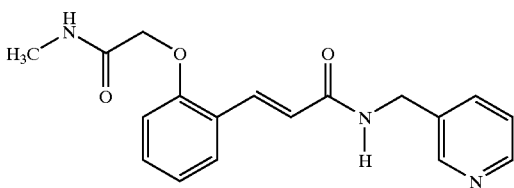

Properties: mp 146–150° C. (methanol/ethyl acetate); ¹H-NMR (CDCl₃) δ: 2.87 (3H, d, J=4.9 Hz), 4.51 (2H, s), 4.58 (2H, d, J=5.9 Hz), 6.53 (1H, d, J=15.7 Hz), 6.66–6.71 (2H, m), 6.83 (1H, d, J=8.2 Hz), 6.96–7.03 (1H, m), 7.23–7.37 (2H, m), 7.48–7.53 (1H, m), 7.69 (1H, brd, J=7.9 Hz), 8.00 (1H, d, J=15.7 Hz), 8.48–8.50 (1H, m), 8.55 (1H, brs).

EXAMPLE 49

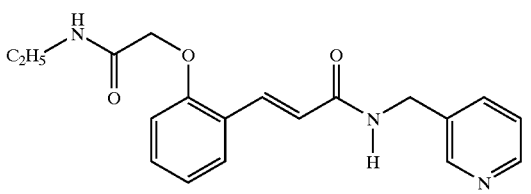

Properties: mp 156.6–157.5° C. (ethyl acetate/dichloromethane); ¹H-NMR (CDCl₃) δ: 1.13 (3H, t, J=7.2 Hz), 3.26–3.40 (2H, m), 4.46 (2H, s), 4.55 (2H, d, J=5.9 Hz), 6.58 (1H, d, J=15.8 Hz), 6.71–6.76 (1H, m), 6.81 (1H, d, J=8.2 Hz), 6.94–7.01 (1H, m), 7.07–7.13 (1H, m), 7.20–7.35 (2H, m), 7.46–7.51 (1H, m), 7.67 (1H, brd, J=8.0 Hz), 7.98 (1H, d, J=15.8 Hz), 8.46 (1H, dd, J=4.8, 1.5 Hz), 8.52 (1H, d, J=1.9 Hz).

EXAMPLE 50

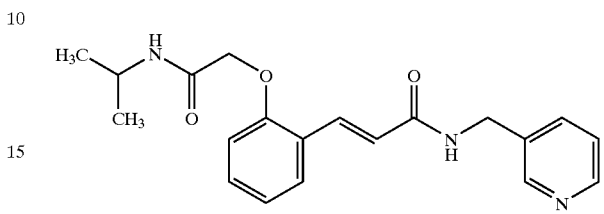

Properties: mp 175–177° C. (ethyl acetate/dichloromethane); ¹H-NMR (CDCl₃) δ: 1.16 (6H, d, J=6.6 Hz), 4.14 (1H, dsept, J=7.9 Hz, 6.6 Hz), 4.49 (2H, s), 4.59 (2H, d, J=5.9 Hz), 6.34–6.39 (1H, m), 6.50–6.58 (1H, m), 6.54 (1H, d, J=15.7 Hz), 6.83 (1H, d, J=8.2 Hz), 7.01 (1H, t, J=7.5 Hz), 7.23–7.37 (2H, m), 7.48–7.53 (1H, m), 7.67–7.72 (1H, m), 7.99 (1H, d, J=15.7 Hz), 8.49–8.52 (1H, m), 8.55–8.56 (1H, m).

EXAMPLE 51

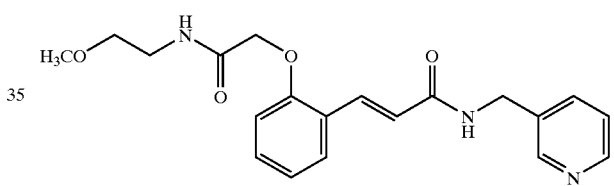

Properties: mp 147–149° C. (ethyl acetate/dichloromethane); ¹H-NMR (CDCl₃) δ: 3.25 (3H, s), 3.45–3.55 (4H, m), 4.55 (2H, s), 4.58 (2H, d, J=6.0 Hz), 6.62 (1H, d, J=15.8 Hz), 6.84–7.07 (4H, m), 7.23–7.38 (2H, m), 7.44–7.50 (1H, m), 7.67–7.74 (1H, m), 7.86 (1H, d, J=15.8 Hz), 8.50–8.54 (1H, m), 8.56–8.58 (1H, m).

EXAMPLE 52

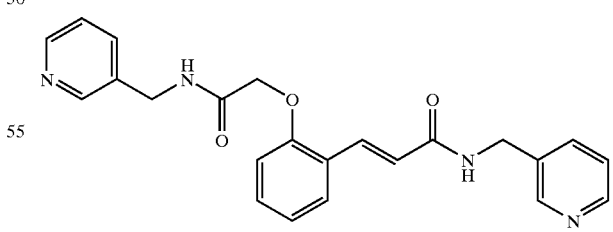

Properties: solid; ¹H-NMR (CDCl₃) δ: 4.53 (2H, d, J=6.1 Hz), 4.54 (2H, d, J=5.9 Hz), 4.59 (2H, s), 6.46 (1H, d, J=15.7 Hz), 6.47–6.52 (1H, m), 6.85 (1H, d, J=8.3 Hz), 7.01 (1H, t, J=7.4 Hz), 7.19–7.37 (4H, m), 7.46–7.50 (1H, m), 7.58–7.68 (2H, m), 7.97 (1H, d, J=15.7 Hz), 8.44–8.53 (4H, m).

EXAMPLE 53

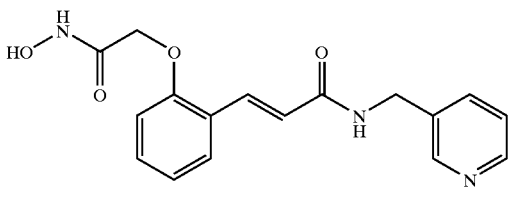

Properties: mp 161–170° C. (methanol); $^1$H-NMR (DMSO-d$_6$) δ: 4.42 (2H, d, J=5.8 Hz), 4.54 (2H, s), 6.65 (1H, d, J=16.0 Hz), 6.94–7.05 (2H, m), 7.30–7.40 (2H, m), 7.53–7.58 (1H, m), 7.67–7.73 (1H, m), 7.80 (1H, d, J=16.0 Hz), 8.45–8.49 (1H, m), 8.52–8.54 (1H, m), 8.64–8.70 (1H, br), 9.05 (1H, brs), 10.89 (1H, brs).

EXAMPLE 54

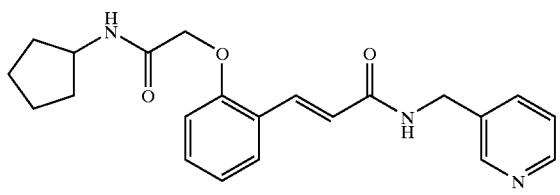

Properties: mp 171.7–175.5° C. (ethyl acetate/chloroform/hexane); $^1$H-NMR (DMSO-d$_6$) δ: 1.30–1.90 (8H, m), 3.97–4.14 (1H, m), 4.42 (2H, d, J=5.9 Hz), 4.56 (2H, s), 6.68 (1H, d, J=16.0 Hz), 6.90 (1H, d, J=8.2 Hz), 7.00 (1H, t, J=7.4 Hz), 7.29–7.40 (2H, m), 7.53–7.58 (1H, m), 7.67–7.73 (1H, m), 7.80 (1H, d, J=16.0 Hz), 8.00 (1H, brd), 8.45–8.49 (1H, m), 8.52–8.54 (1H, m), 8.67 (1H, brt, J=5.9 Hz).

EXAMPLE 55

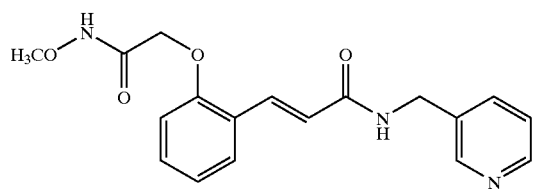

Properties: mp 171.0–173.8° C. (methanol/chloroform); $^1$H-NM (DMSO-d$_6$) δ: 3.63 (3H, s), 4.43 (2H, d, J=5.9 Hz), 4.57 (2H, s), 6.67 (2H, d, J=16.0 Hz), 6.93–7.06 (2H, m), 7.29–7.39 (2H, m), 7.53–7.59 (1H, m), 7.67–7.73 (1H, m), 7.81 (1H, d, J=16.0 Hz), 8.45–8.48 (1H, m), 8.53 (1H, brs), 8.65 (1H, brt, J=5.9 Hz).

EXAMPLE 56

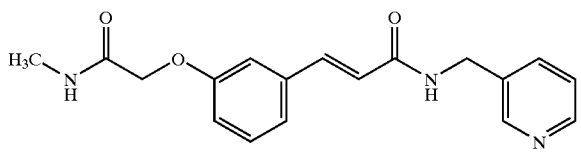

Properties: mp 172° C. (dichloromethane/methanol); $^1$H-NMR (DMSO-d$_6$) δ: 2.66 (3H, d, J=4.7 Hz), 4.43 (2H, d, J=5.9 Hz), 4.50 (2H, s), 6.67 (1H, d, J=15.8 Hz), 6.98 (1H, m) 7.00 (1H, m), 7.17–7.21 (2H, m), 7.31–7.40 (2H, m), 7.44 (1H, d, J=15.8 Hz), 8.04 (1H, brs), 8.45–8.53 (2H, m), 8.70 (1H, t, J=5.9 Hz).

EXAMPLE 57

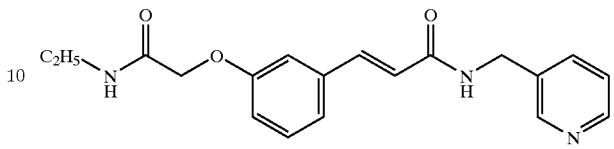

Properties: mp 152–154° C.; $^1$H-NMR (DMSO-d$_6$) δ: 1.04 (3H, t, J=7.2 Hz), 3.16 (2H, m), 4.43 (2H, d, J=5.9 Hz), 4.49 (2H, s), 6.67 (1H, d, J=15.8 Hz), 6.98 (1H, m), 7.16–7.20 (2H, m), 7.31–7.38 (2H, m), 7.44 (1H, d, J=15.8 Hz), 7.67–7.73 (1H, m), 8.12 (1H, m), 8.45–8.53 (2H, m), 8.71 (1H, t, J=5.9 Hz).

EXAMPLE 58

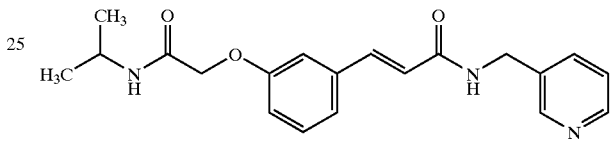

Properties: mp 133–134° C.; $^1$H-NMR (DMSO-d$_6$) δ: 1.09 (6H, d, J=6.6 Hz), 3.70 (1H, m), 4.42 (2H, d, J=5.9 Hz), 4.47 (2H, s), 6.67 (1H, d, J=15.7 Hz), 6.97 (1H, m), 7.15–7.20 (2H, m), 7.30–7.40 (2H, m), 7.43 (1H, d, J=15.7 Hz), 7.70 (1H, m), 7.89 (1H, brd, J=8.0 Hz), 8.45–8.53 (2H, m), 8.69 (1H, t, J=5.9 Hz).

EXAMPLE 59

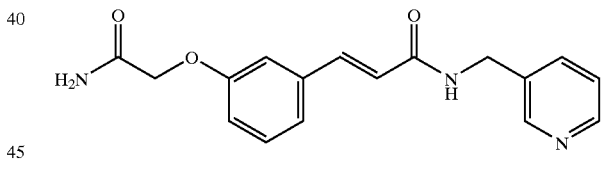

Properties: mp 180–181° C. (ethyl acetate/methanol); $^1$H-NMR (DMSO-d$_6$) δ: 4.42 (2H, d, J=6.1 Hz), 4.46 (2H, s), 6.66 (1H, d, J=15.0 Hz), 6.97 (1H, m), 7.15–7.19 (2H, m), 7.30–7.54 (4H, m), 7.51 (1H, d, J=15.0 Hz), 7.70 (1H, m), 8.45–8.52 (2H, m), 8.90 (1H, m).

EXAMPLE 60

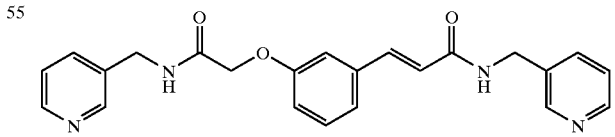

Properties: mp 127–130° C. (dichloromethane/hexane); $^1$H-NMR (DMSO-d$_6$) δ: 4.37 (2H, d, J=6.1 Hz), 4.43 (2H, d, J=5.8 Hz), 4.61 (2H, s), 6.66 (1H, d, J=15.8 Hz), 6.99 (1H, m), 7.19 (2H, m), 7.28–7.38 (3H, m), 7.44 (1H, d, J=15.8 Hz), 7.61–7.72 (2H, m), 8.41–8.54 (4H, m), 8.71–8.73 (2H, m).

EXAMPLE 61

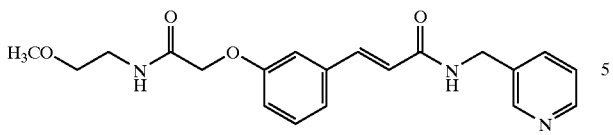

Properties: mp 112° C.; $^1$H-NMR (DMSO-d$_6$) δ: 3.23 (3H, s), 3.28–3.40 (4H, m), 4.43 (2H, d, J=5.8 Hz), 4.52 (2H, s), 6.67 (1H, d, J=15.9 Hz), 6.98 (1H, m), 7.16–7.21 (2H, m), 7.31–7.39 (2H, m), 7.44 (1H, d, J=15.9 Hz), 7.70 (1H, m), 8.13 (1H, m), 8.47 (1H, m), 8.53 (1H, m), 8.71 (1H, m).

EXAMPLE 62

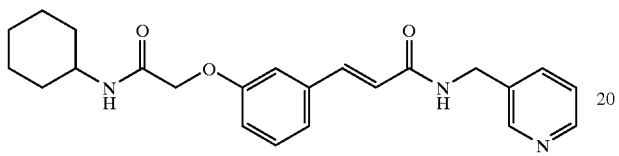

Properties: amorphous; $^1$H-NMR (CDCl$_3$) δ: 1.09–1.48 (5H, m), 1.59–1.71 (3H, m), 1.88–1.94 (2H, m), 3.87 (1H, m), 4.45 (2H, s), 4.61 (2H, d, J=6.0 Hz), 6.32–6.40 (2H, m), 6.44 (1H, d, J=15.6 Hz), 6.92 (1H, m), 7.02 (1H, m), 7.16 (1H, m), 7.25–7.36 (2H, m), 7.64 (1H, d, J=15.6 Hz), 7.70 (1H, m), 8.51–8.59 (2H, m).

EXAMPLE 63

Synthesis of (E)-3-[4-[(Morpholinocarbonyl) methoxy]phenyl]-N-(3-pyridylmethyl)-2-propenoic Acid Amide

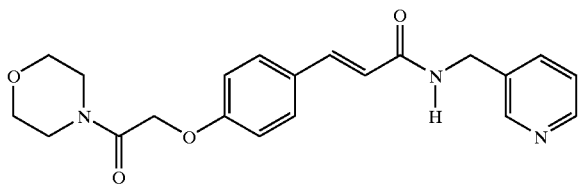

697 mg of [4-[(E)-2-[N-(3-pyridylmethyl)carbamoyl] ethenyl]phenoxy]acetic acid hydrochloride from Example 36 and 0.20 ml of morpholine were dissolved in 6 ml dimethylformamide, and then stirred with 0.36 ml diethylphosphoryl cyanide and subsequently with 0.60 ml triethylamine on ice for 1.5 hours. After addition of water, the reaction mixture was extracted with ethyl acetate, washed with brine, and then dried over magnesium sulfate. The solvent was evaporated under reduced pressure to give a residue, which was then purified via column chromatography on silica gel (dichloromethane:methanol=15:1), followed by recrystallization, to provide the compound of interest (65 mg, 8%).

Properties: mp 213.6° C. (acetone); $^1$H-NMR (DMSO-d$_6$) δ: 3.40–3.70 (8H, m), 4.41 (2H, d, J=5.9 Hz), 4.88 (2H, s), 6.52 (1H, d, J=15.8 Hz), 6.96 (2H, d, J=8.7 Hz), 7.32–7.37 (1H, m), 7.42 (1H, d, J=15.8 Hz), 7.51 (2H, d, J=8.7 Hz), 7.65–7.73 (1H, m), 8.44–8.48 (1H, m), 8.51–8.53 (1H, m), 8.60 (1H, t, J=5.9 Hz).

EXAMPLE 64

The following compound was obtained in the same manner as described in Example 63.

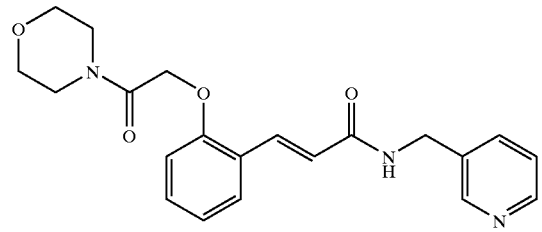

Properties: oil; $^1$H-NMR (CDCl$_3$) δ: 3.55–3.68 (8H, m), 4.57 (2H, d, J=6.0 Hz), 4.74 (2H, s), 6.61–6.68 (1H, br), 6.73 (1H, d, J=15.8 Hz), 6.89–7.02 (2H, m), 7.15–7.34 (2H, m), 7.43–7.49 (1H, m), 7.66–7.71 (1H, m), 7.91 (1H, d, J=15.8 Hz), 8.50–8.55 (2H, m).

EXAMPLE 65

Synthesis of (E)-3-[2-[[N-(Methyl)thiocarbamoyl] methoxy]phenyl]-N-(3-pyridylmethyl)-2-propenoic Acid Thioamide

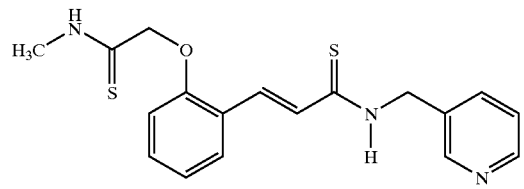

A mixture of (E)-3-[2-[(methylcarbamoyl)methoxy] phenyl]-N-(3-pyridylmethyl)-2-propenoic acid amide from Example 48 (650 mg), Lawesson reagent (849 mg) and xylene (4 ml)/chloroform (4 ml) was heated at reflux for 2 hours. After evaporation of the solvent under reduced pressure, saturated aqueous sodium bicarbonate was added to the reaction mixture, which was then extracted with chloroform, washed with water, and dried over sodium sulfate. The solvent was evaporated under reduced pressure to give a residue, which was then purified via column chromatography on silica gel (chloroform:hexane:methanol=50:10:1), followed by recrystallization, to provide the compound of interest (237 mg, 33%).

Properties: mp 193–195° C. (chloroform); $^1$H-NMR (DMSO-d$_6$) δ: 3.02 (3H, d, J=4.5 Hz), 4.94 (2H, d, J=4.7 Hz), 4.95 (2H, s), 6.83 (1H, d, J=8.2 Hz), 7.04 (1H, t, J=7.5 Hz), 7.16 (1H, d, J=15.6 Hz), 7.31–7.43 (2H, m), 7.58–7.62 (1H, m), 7.75–7.79 (1H, m), 8.11 (1H, d, 15.6 Hz), 8.50 (1H, dd, J=4.7, 1.4 Hz), 8.59 (1H, d, J=1.6 Hz), 9.95–10.15 (1H, br), 10.53 (1H, brt).

EXAMPLES 66 TO 71

The following compounds were obtained in the same manner as described in Example 65.

EXAMPLE 66

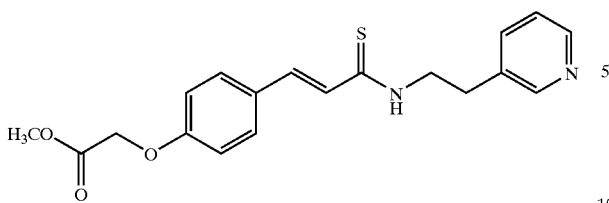

Properties: mp 182.1–184.0° C. (ethyl acetate/hexane); $^1$H-NMR (DMSO-$d_6$) δ: 2.98 (2H, t, J=7.2 Hz), 3.71 (3H, s), 3.85–3.93 (2H, m), 4.86 (2H, s), 6.95 (1H, d, 15.5 Hz), 6.98 (2H, d, J=8.8 Hz), 7.30–7.38 (1H, m), 7.53 (2H, d, J=8.8 Hz), 7.66 (1H, d, 15.5 Hz), 7.66–7.73 (1H, m), 8.42–8.46 (1H, m), 8.48–8.50 (1H, m), 10.09–10.30 (1H, br).

EXAMPLE 67

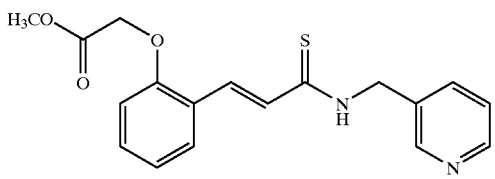

Properties: mp 127–132° C. (ethyl acetate); $^1$H-NMR (CDCl$_3$) δ: 3.79 (3H, s), 4.70 (2H, s), 5.07 (2H, d, J=5.6 Hz), 6.77 (1H, d, J=8.1 Hz), 6.96–7.05 (1H, m), 7.25–7.31 (2H, m), 7.37 (1H, d, 15.5 Hz), 7.48–7.54 (1H, m), 7.75–7.85 (1H, m), 7.85–8.00 (1H, br), 8.01 (1H, d, 15.5 Hz), 8.53–8.57 (1H, m), 8.62 (1H, brs).

EXAMPLE 68

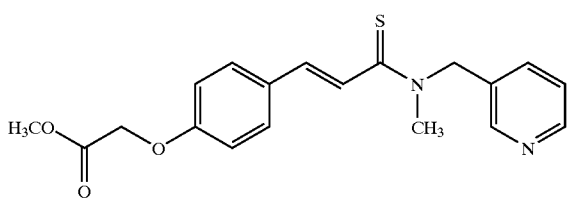

Properties: mp 117.1–119.0° C. (ethyl acetate/hexane); $^1$H-NMR (DMSO-$d_6$, 100° C.) δ: 2.93 (3H, s), 3.71 (3H, s), 4.77 (2H, s), 5.25–5.35 (2H, br), 6.95 (2H, d, J=8.8 Hz), 7.28 (1H, d, J=15.0 Hz), 7.33–7.38 (1H, m), 7.58 (2H, d, J=8.8 Hz), 7.60–7.70 (1H, m), 7.65 (1H, d, J=15.0 Hz), 8.46–8.50 (1H, m), 8.54 (1H, brs).

EXAMPLE 69

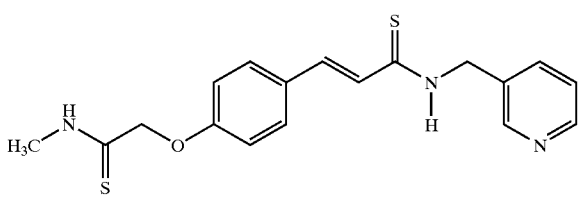

Properties: solid; $^1$H-NMR (CDCl$_3$) δ: 3.28 (3H, d, J=4.9 Hz), 4.92 (2H, s), 5.05 (2H, d, J=5.5 Hz), 6.76 (1H, d, J=15.3 Hz), 6.92 (2H, d, J=8.8 Hz), 7.28–7.34 (1H, m), 7.50 (2H, d, J=8.8 Hz), 7.53–7.59 (1H, br), 7.71–7.79 (1H, m), 7.83 (1H, d, J=15.3 Hz), 8.11–8.47 (1H, br), 8.55–8.61 (2H, m).

EXAMPLE 70

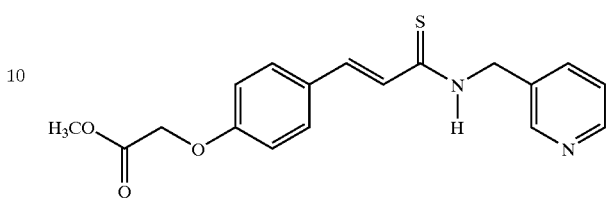

Properties: solid; $^1$H-NMR (CDCl$_3$) δ: 3.81 (3H, s), 4.66 (2H, s), 5.05 (2H, d, J=5.5 Hz), 6.74 (1H, d, J=15.3 Hz), 6.89 (2H, d, J=8.8 Hz), 7.27–7.34 (1H, m), 7.48 (2H, d, J=8.8 Hz), 7.57–7.63 (1H, br), 7.72–7.79 (1H, m), 7.83 (1H, d, J=15.3 Hz), 8.54–8.61 (2H, m).

EXAMPLE 71

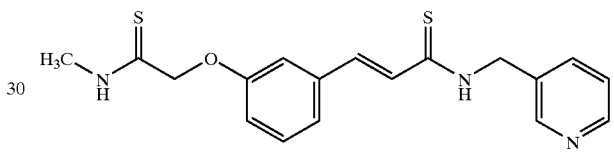

Properties: mp 178–180° C.; $^1$H-NMR (DMSO-$d_6$) δ: 3.05 (3H, d, J=4.6 Hz), 4.91 (2H, s), 4.92 (2H, d, J=7.6 Hz), 7.04 (1H, m), 7.14 (1H, d, J=15.4 Hz), 7.21–7.43 (4H, m), 7.69 (1H, d, J=15.4 Hz), 7.75 (1H, m), 8.50 (1H, m), 8.59 (1H, m), 10.1 (1H, brs), 10.6 (1H, m).

EXAMPLES 72 AND 73

The following compounds shown in Example 72 and 73 were obtained by hydrolysis of the compounds from Example 27 and 16, respectively.

EXAMPLE 72

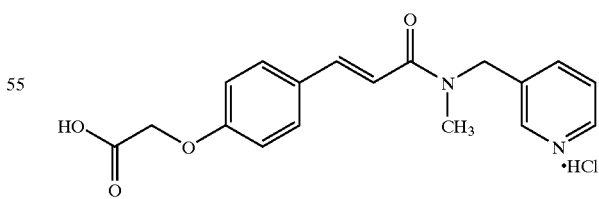

Properties: mp 150° C. (dec.) (acetone/water); $^1$H-NMR (DMSO-$d_6$, 100° C.) δ: 3.12 (3H, s), 4.67 (2H, s), 4.80 (2H, s), 6.94 (2H, d, J=8.8 Hz), 7.01 (1H, d, J=15.4 Hz), 7.49 (1H, d, J=15.4 Hz), 7.59 (2H, d, J=8.8 Hz), 7.75–7.83 (1H, m), 8.15–8.20 (1H, m), 8.65–8.70 (2H, m).

EXAMPLE 73

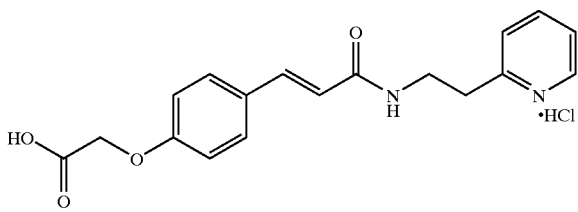

Properties: mp 107° C. (dec.) (water/acetone); $^1$H-NMR (DMSO-$d_6$) δ: 3.26 (2H, t, J=6.4 Hz), 3.65 (2H, q, J=6.4 Hz), 4.72 (2H, s), 6.46 (1H, d, J=15.9 Hz), 6.94 (2H, d, J=8.7 Hz), 7.32 (1H, d, J=15.8 Hz), 7.48 (2H, d, J=8.7 Hz), 7.97 (2H, m), 8.49 (2H, m), 8.81 (1H, d, J=4.9 Hz).

EXAMPLE 74

The following compound was obtained in the same manner as described in Examples 1 and 36.

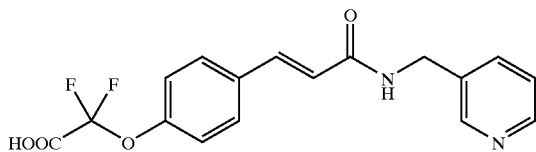

Properties: solid; $^1$H-NMR(DMSO-$d_6$) δ: 4.46 (2H, d, J=5.9 Hz), 6.65 (1H, d, J=15.9 Hz), 7.25 (2H, d, J=8.5 Hz), 7.48 (1H, d, J=15.9 Hz), 7.48–7.55 (1H, m), 8.69 (2H, d, J=8.5 Hz), 7.85–7.89 (1H, m), 8.55 (1H, dd, J=1.5 Hz, 4.9 Hz), 8.60 (1H, d, J=1.5 Hz), 8.76(1H, t, J=5.9 Hz).

EXAMPLE 75

Synthesis of 3-[4-[(E)-2-[N-(3-Pyridylmethyl) carbamoyl]ethenyl]phenyl]propionic Acid Hydrochloride

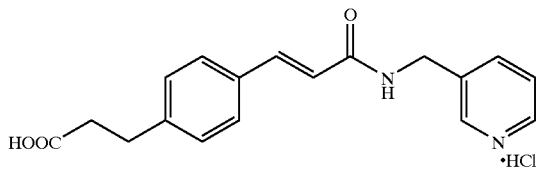

A suspension of 4-formylcinnamic acid (10.0 g), dimethyl sulfate (5.9 ml) and potassium carbonate (11.8 g) in 100 ml dimethylformamide was stirred at room temperature for 17 hours. After removal of inorganic salts by filtration, saturated aqueous sodium bicarbonate was added to the reaction mixture, which was then extracted twice with ethyl acetate. The organic layer was washed with saturated aqueous sodium bicarbonate and brine, and dried over sodium sulfate. The drying agent was filtered off and the filtrate was evaporated and dried under reduced pressure to give methyl 4-formylcinnamate (9.78 g, 91%) as a pale yellow solid.

A suspension of methyl 4-formylcinnamate (3.23 g) and 10% palladium-carbon (323 mg) in 30 ml ethyl acetate was stirred under hydrogen atmosphere at room temperature until 760 ml hydrogen was consumed. The palladium-carbon was filtered onto Celite. The filtrate was evaporated and dried under reduced pressure to give a colorless solid (3.29 g), which was then purified via column chromatography on silica gel (hexane:ethyl acetate=7:1) to provide methyl 4-hydroxymethylhydrocinnamate (2.42 g, 73%) and methyl 4-formylhydrocinnamate (638 mg, 20%) as colorless solids, respectively.

A suspension of methyl 4-hydroxymethylhydrocinnamate (2.34 g) and manganese dioxide (21.0 g) in 40 ml dichloromethane was stirred at room temperature for 17 hours. Manganese dioxide was filtered off onto Celite. The filtrate was evaporated and dried under reduced pressure to give methyl 4-formylhydrocinnamate (2.11 g, 91%) as a colorless solid.

A solution of methyl 4-formylhydrocinnamate (2.30 g), malonic acid (2.50 g) and piperidine (0.1 ml) in 12 ml pyridine was stirred at 100° C. for 2 hours, and subsequently at 140° C. for 2 hours. After addition of 100 ml ice-cold water, 210 ml of 0.5 mol/l hydrochloric acid was added dropwise to the reaction mixture to precipitate a solid, which was then filtered, washed with water, and dried by heating under reduced pressure to give 4-[2-(methoxycarbonyl) ethyl]cinnamic acid (2.38 g, 84%) as a colorless solid.

A solution of 4-[2-(methoxycarbonyl)ethyl]cinnamic acid (2.38 g), thionyl chloride (0.82 ml) and dimethylformamide (2 drops) in 50 ml dichloromethane was heated at reflux for 30 minutes. After evaporation of dichloromethane and low-boiling components, the residue was dried under reduced pressure to give a solid, which was then dissolved in 20 ml ethyl acetate and stirred with 1.10 g of 3-picolylamine in 20 ml ethyl acetate at room temperature for 30 minutes. After the reaction mixture was washed with saturated aqueous sodium bicarbonate, the resulting aqueous layer was extracted with 40 ml ethyl acetate. The combined organic layers were washed with saturated aqueous sodium carbonate and brine, and then dried over sodium sulfate. The drying agent was filtered off and the solvent was evaporated to give crude crystals (3.23 g), which were then recrystallized from ethyl acetate to provide methyl 3-[4-[(E)-2-[N-(3-pyridylmethyl)carbamoyl]ethenyl]phenyl]propionate (2.82 g, 86%) as colorless plate crystals.

Properties: solid; $^1$H-NMR(CDCl$_3$) δ: 2.63 (2H, t, J=8 Hz), 2.95 (2H, t, J=8 Hz), 3.66 (3H, s), 4.57 (2H, d, J=6 Hz), 6.37–6.45 (1H, m), 6.41 (1H, d, J=16 Hz), 7.19 (2H, d, J=8 Hz), 7.22–7.29 (1H, m), 7.41 (2H, d, J=8 Hz), 7.65 (1H, d, J=16 Hz), 7.66–7.71 (1H, m), 8.50–8.55 (2H, m).

A solution of methyl 3-[4-[(E)-2-[N-(3-pyridylmethyl) carbamoyl]ethenyl]phenyl]propionate (2.27 g) in aqueous methanol was stirred with 1.93 g of potassium carbonate at 100° C. for 30 minutes. After the reaction mixture was mixed with 70 ml water, 70 ml of 0.2 mol/l sulfuric acid was added thereto, on ice, to precipitate a solid, which was then filtered and dried under reduced pressure at 100° C. to provide 3-[4-(E)-2-[N-(3-pyridylmethyl)carbamoyl] ethenyl]phenyl]propionic acid (2.16 g, 100%) as a colorless solid.

Properties: solid; $^1$H-NMR(DMSO-$d_6$) δ: 2.55 (2H, t, J=7.4 Hz), 2.84 (2H, t, J=7.4 Hz), 4.43 (2H, d, J=5.9 Hz), 6.64 (1H, d, J=15.9 Hz), 7.28 (2H, d, J=8.1 Hz), 7.37 (1H, dd, J=4.8 Hz, 7.8 Hz), 7.46 (1H, d, J=15.9 Hz), 7.49 (2H, d, J=8.1 Hz), 7.66–7.73 (1H, m), 8.47 (1H, dd, J=1.6 Hz, 4.8 Hz), 8.53 (1H, d, J=2.0 Hz), 8.68 (1H, t, J=5.9 Hz).

1.55 g of 3-[4-(E)-2-[N-(3-pyridylmethyl)carbamoyl] ethenyl]phenyl]propionic acid was dissolved in 50 ml of 0.1 mol/l hydrochloric acid. After evaporation of water, the residue was azeotroped with toluene and dried under reduced pressure at 100° C. to give 3-[4-[(E)-2-[N-(3-pyridylmethyl)carbamoyl]ethenyl]phenyl]propionic acid hydrochloride of interest (1.53 g, 88%) as a pale yellow solid.

Properties: mp 212° C. (acetone/water); ¹H-NMR (DMSO-d₆) δ: 2.56 (2H, t, J=7.4 Hz), 2.85 (2H, t, J=7.4 Hz), 4.60 (2H, d, J=5.8 Hz), 6.72 (1H, d, J=15.8 Hz), 7.28 (2H, d, J=8.1 Hz), 7.47 (1H, d, J=15.8 Hz), 7.50 (2H, d, J=8.1 Hz), 8.03 (1H, dd, J=5.6 Hz, 8.0 Hz), 8.46–8.50 (1H, m), 8.82–8.87 (2H, m), 9.08 (1H, t, J=5.8 Hz).

EXAMPLE 76

The following compound was obtained in the same manner as described in Example 75.

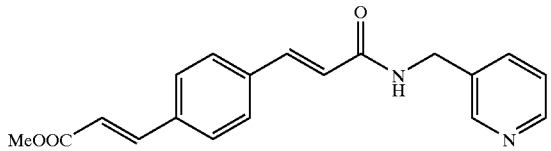

Properties: solid; ¹H-NMR(CDCl₃) δ: 3.81 (3H, s), 4.61 (2H, d, J=6 Hz), 6.02–6.37 (1H, m), 6.46 (2H, d, J=16 Hz), 7.25–7.31 (1H, m), 7.51 (4H, s), 7.59–7.72 (1H, m), 7.67 (1H, d, J=16 Hz), 7.68 (1H, d, J=16 Hz), 8.54 (1H, dd, J=2 Hz, 5 Hz), 8.58 (1H, d, J=2 Hz).

EXAMPLE 77

The following compound was obtained in the same manner as described in Example 75.

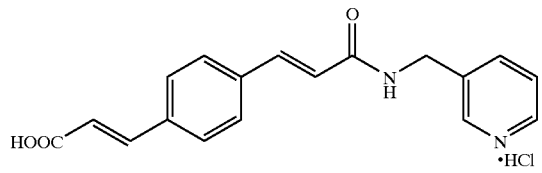

Properties: solid; ¹H-NMR(DMSO-d₆) δ: 4.59 (2H, d, J=5.7 Hz), 6.58 (1H, d, J=16.0 Hz), 6.80 (1H, d, J=15.9 Hz), 7.47–7.76 (6H, m), 7.97 (1H, dd, J=5.6 Hz, 7.9 Hz), 7.39–7.43 (1H, m), 8.78–8.83 (2H, m), 9.02 (1H, t, J=5.7 Hz).

EXAMPLE 78

The following compound was obtained in the same manner as described in Example 75.

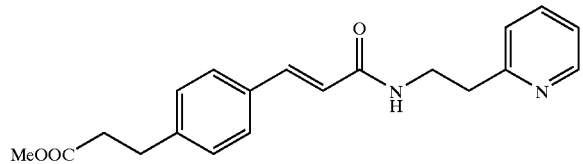

Properties: mp. 117–118° C. (ethyl acetate); ¹H-NMR (CDCl₃) δ: 2.63 (2H, t, J=7.2 Hz), 2.96 (2H, t, J=7.5 Hz), 3.06 (2H, t, J=6.4 Hz), 3.67 (3H, s), 3.76–3.85 (2H, m), 6.35 (1H, d, J=15.6 Hz), 6.71 (1H, br), 7.14–7.21 (2H, m), 7.19 (2H, d, J=8.1 Hz), 7.42 (2H, d, J=8.1 Hz), 7.57 (1H, d, J=15.6 Hz), 7.59–7.67 (1H, m), 8.54–8.58 (1H, m).

EXAMPLE 79

The following compound was obtained in the same manner as described in Example 75.

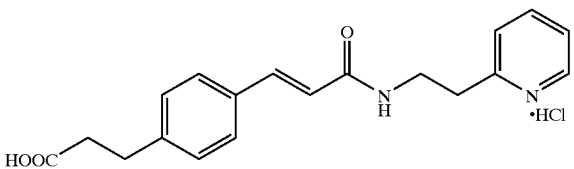

Properties: mp. 185–186° C. (acetone/water); ¹H-NMR (CDCl₃) δ: 2.52 (2H, t, J=7.2 Hz), 2.83 (2H, t, J=7.3 Hz), 3.18 (2H, t, J=6.5 Hz), 3.58–3.67 (2H, m), 6.52 (1H, d, J=15.8 Hz), 7.26 (2H, d, J=8.2 Hz), 7.34 (1H, d, J=15.8 Hz), 7.45 (2H, d, J=8.2 Hz), 7.79–7.88 (2H, m), 8.30–8.43 (2H, m), 8.79 (1H, d, J=5.6 Hz).

EXAMPLE 80

Synthesis of Methyl 3-Hydroxy-3-[4-[2-[-(3-pyridylmethyl)carbamoyl]ethenyl]phenyl]propionate

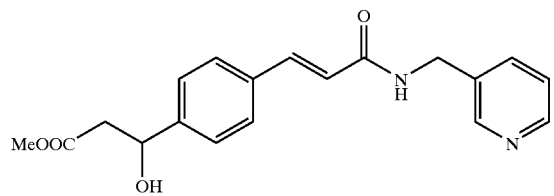

A suspension of 4-formylcinnamic acid (1.76 g), p-methoxybenzyl chloride (1.63 ml) and potassium carbonate (2.76 g) in 20 ml dimethylformamide was stirred at 80° C. for 7 hours, and then allowed to cool. The reaction mixture was extracted with ethyl acetate and washed with water. The combined organic layers were dried over magnesium sulfate. The drying agent was filtered off and the filtrate was evaporated under reduced pressure and dried to give p-anisyl 4formylcinnamate of interest (2.96 g, 100%) as a pale yellow solid.

Next, 296 mg of p-anisyl 4-formylcinnamate and 0.14 ml of methyl bromoacetate were dissolved in 4 ml benzene, and mixed with 95 mg of zinc powder to form a suspension, followed by heating under a stream of argon for 5 hours. The reaction mixture was allowed to cool, mixed with 10% sulfuric acid, extracted with ether and then washed with 5% sulfuric acid. The organic layer was washed with 10% aqueous sodium carbonate, and dried over magnesium sulfate. The drying agent was filtered off and the filtrate was evaporated under reduced pressure and dried to give p-anisyl 4-[1-hydroxy-2-(methoxycarbonyl)ethyl]-cinnamate of interest (51 mg, 14%) as a pale yellow liquid.

44 mg of p-anisyl 4-[1-hydroxy-2-(methoxycarbonyl) ethyl]cinnamate was dissolved in 0.1 ml anisole, and then treated with 0.1 ml trifluoroacetic acid on ice for 30 minutes to give 4-[1-hydroxy-2-(methoxycarbonyl)ethyl]cinnamic acid (27 mg, 91%) as a white solid.

Finally, 82 mg of 4-[1-hydroxy-2-(methoxycarbonyl) ethyl]cinnamic acid was dissolved in 37 μl 3-(aminomethyl) pyridine and 1 ml dimethylformamide, and then treated with 55 μl diethyl cyanophosphate and 50 μl triethylamine on ice for 1 hour to give methyl 3-hydroxy-3-[4-[2-[N-(3-pyridylmethyl)carbamoyl]ethenyl]phenyl]propionate of interest (17 mg, 15%) as an amorphous solid.

Properties: amorphous; ¹H-NMR(CDCl₃) δ: 2.72–2.76 (2H, m), 3.73 (3H, s), 4.02–4.14 (1H, m), 4.60 (2H, d, J=6.0 Hz), 5.15 (1H, dd, J=5.6 and 7.1 Hz), 6.07 (1H, t, J=5.6 Hz), 6.41 (1H, d, J=15.6 Hz), 7.26–7.32 (1H, m), 7.38 (2H, d, J=8.3 Hz), 7.49 (2H, d, J=8.3 Hz), 7.67 (1H, d, J=15.6 Hz), 7.67–7.71 (1H, m), 8.52–8.58 (2H, m).

EXAMPLE 81

Synthesis of Ethyl [4-[2-Cyano-2-[N-(3-pyridylmethyl)carbamoyl]ethenyl]phenoxy]acetate

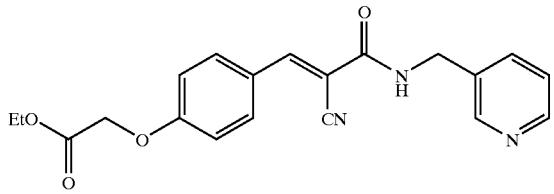

A solution of ethyl (4-formylphenoxy)acetate (1.25 g), 2-cyano-N-(3-pyridylmethyl) acetamide (875 mg) and piperidine (5 drops) in dry dioxane was refluxed under argon atmosphere for 3 days. The reaction mixture was mixed with water and extracted with ethyl acetate. The organic layer was washed with water and brine, and then dried over sodium sulfate. The drying agent was filtered off and the solvent was evaporated to give a residue, which was then purified via column chromatography (chloroform:methanol=50:1) to provide crude crystals (1.67 g). These crystals were recrystallized from hexane/ethyl acetate to give the compound of interest (1.53 g, 83%) as pale yellow needle crystals.

Properties: mp 139–140° C. (hexane/ethyl acetate); $^1$H-NMR(CDCl$_3$) δ: 1.31 (3H, t, J=7.1 Hz), 4.29 (2H, q, J=7.1 Hz), 4.64 (2H, d, J=5.9 Hz), 4.70 (2H, s), 6.88 (1H, t, J=5.9 Hz), 6.99 (2H, d, J=8.9 Hz), 7.34 (1H, dd, J=7.8 Hz, 4.8 Hz), 7.73–7.77 (1H, m), 7.94 (2H, d, J=8.9 Hz), 8.29 (1H, s), 8.57 (1H, dd, J=4.8 Hz, 8.65 (1H, d, J=1.4 Hz).

EXAMPLE 82

Synthesis of Sodium [4-[2-Cyano-2-[N-(3-pyridylmethyl)carbamoyl]ethenyl]phenoxy]acetate

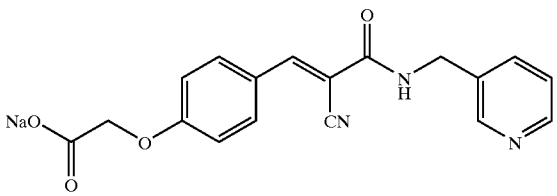

A solution of ethyl [4-[2-cyano-2-[N-(3-pyridylmethyl)carbamoyl]ethenyl]phenoxy]acetate (730 mg) in 30 ml methanol was stirred with 10 ml of 0.2 mol/l aqueous sodium hydroxide at room temperature for 18 hours. After evaporation of methanol, the reaction mixture was mixed with 100 ml water and then extracted with 30 ml ethyl acetate to remove unreacted components. The aqueous layer was concentrated until a solid came out. A part of the resulting solid was filtered, and then dried over diphosphorus pentaoxide by heating under reduced pressure to give the compound of interest (156 mg, 22%) as a pale yellow solid.

Properties: solid; $^1$H-NMR(DMSO-d$_6$) δ: 4.30 (2H, s), 4.36–4.56 (2H, m), 6.99 (2H, d, J=8.9 Hz), 7.36 (1H, dd, J=7.8 Hz, 4.8 Hz), 7.70–7.82 (1H, m), 7.92 (2H, d, J=8.9 Hz), 8.26 (1H, s), 8.46 (1H, dd, J=4.8 Hz, 1.6 Hz), 8.55 (1H, d, J=1.8 Hz), 9.15–9.44 (1H, m).

EXAMPLE 83

Synthesis of [4-[2-Cyano-2-[N-(3-pyridylmethyl)carbamoyl]ethenyl]phenoxy]acetic Acid

The filtrate and the remainder of the solid from Example 82 were dissolved in water (100 ml)/methanol (100 ml), and neutralized with 20 ml of 0.1 mol/l hydrochloric acid. Methanol was evaporated and impurities were removed by extraction with ethyl acetate. The aqueous layer was filtered to remove insoluble components, concentrated to about 50 ml, and then allowed to stand overnight. The precipitated solid was filtered, washed with a small amount of acetone, and then dried by heating under reduced pressure to give the compound of interest (102 mg, 19%) as a pale yellow solid.

Properties: solid; $^1$H-NMR(DMSO-d$_6$) δ: 4.52 (2H, d, J=5.7 Hz), 4.83 (2H, s), 7.12 (2H, d, J=8.9 Hz), 7.70 (1H, dd, J=7.9 Hz, 5.2 Hz), 7.98 (2H, d, J=8.9 Hz), 8.09–8.23 (1H, m), 8.31 (1H, s), 8.60–8.70 (1H, m), 8.74 (1H, d, J=1.4 Hz), 9.31 (1H, t, J=5.7 Hz).

EXAMPLE 84

The following compound was obtained in the same manner as described in Example 81.

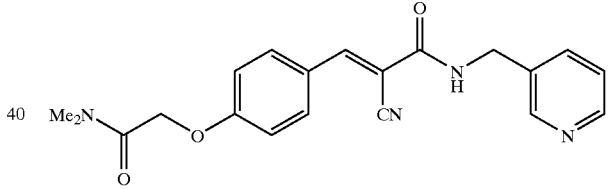

Properties: mp 179–182° C. (methanol/ethyl acetate); $^1$H-NMR(DMSO-d$_6$) δ: 2.85 (3H, s), 3.00 (3H, s), 4.44 (2H, d, J=5.8 Hz), 4.97 (2H, s), 7.09 (2H, d, J=8.9 Hz), 7.37 (1H, dd, J=7.8 Hz, 4.8 Hz), 7.01–7.77 (1H, m), 7.96 (2H, d, J=8.9 Hz), 8.16 (1H, s), 8.48 (1H, dd, J=4.8 Hz, 1.6 Hz), 8.56 (1H, d, J=1.8 Hz), 9.00 (1H, t, J=5.8 Hz).

EXAMPLE 85

Synthesis of Ethyl [4-[(E)-1-Methyl-2-[N-(3-Pyridylmethyl)carbamoyl]ethenyl]phenoxy]acetate

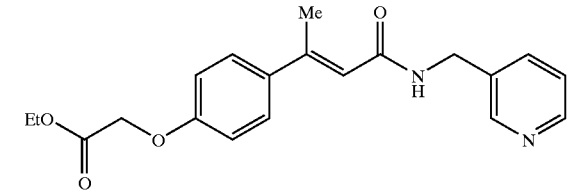

4 ml of chloromethyl methyl ether was added dropwise to a solution of 4'-hydroxyacetophenone (5.44 g) and diisopropylethylamine (10 ml) in 40 ml dinethylformamide at room temperature and stirred at room temperature for 3 hours. After addition of 2 mol/l hydrochloric acid, the reaction mixture was extracted with ethyl acetate. The organic layer was washed with water and dried over magnesium sulfate. The drying agent was filtered off and the solvent was evaporated to give a residue, which was then purified via column chromatography on silica gel (hexane:ethyl acetate= 7:1) to provide 4'-(methoxymethoxy)acetophenone (6.73 g, 93%) as a colorless oil.

9 ml of ethyl diethylphosphonoacetate was added dropwise to a suspension of 60% sodium hydride in oil (1.93 g) in 40 ml tetrahydrofuran and stirred at room temperature for 30 minutes. A solution of 4'-(methoxymethoxy) acetophenone (6.70 g) in 40 ml tetrahydrofuran was added dropwise to the reaction mixture, followed by stirring at room temperature for 17 hours and subsequently at reflux for 4 days. The solvent was evaporated, and the reaction mixture was mixed with water and then extracted with ethyl acetate. The resulting organic layer was washed with water and brine, and then dried over magnesium sulfate. The drying agent was filtered off and the solvent was evaporated to give a residue, which was then purified via column chromatography on silica gel (hexane:ethyl acetate=10:1) to provide ethyl (E)-3-[4-(methoxymethoxy)phenyl]-2-butenoate (3.91 g, 42%) as a colorless oil and ethyl (Z)-3-[4-(methoxymethoxy)phenyl]-2-butenoate (425 mg, 4.6%) as a colorless oil, respectively.

A solution of ethyl (E)-3-[4-(methoxymethoxy)phenyl]-2-butenoate (3.79 g) in methanol was stirred with 0.76 mol/l aqueous sodium hydroxide at room temperature for 2 hours. Methanol was evaporated and 0.45 mol/l hydrochloric acid was added dropwise to the residue to precipitate a solid, which was then filtered, washed with water, and dried by heating under reduced pressure to give (E)-3-[4-(methoxymethoxy)phenyl]-2-butenoic acid (2.36 g, 70%) as a colorless solid.

1.11 g of (E)-3-[4-(methoxymethoxy)phenyl]-2-butenoic acid was dissolved in 11 ml dimethylformamide and reacted with 0.56 ml 3-(aminomethyl)pyridine, 0.93 ml diethyl cyanophosphate and 0.77 ml triethylamine at room temperature for 4 hours. The reaction mixture was extracted with ethyl acetate and 40 ml water, and the aqueous layer was further extracted with ethyl acetate. The combined ethyl acetate layers were washed with water and brine, and dried over anhydrous magnesium sulfate. The drying agent was filtered off and the solvent was evaporated to give a crude product, which was used for the subsequent reaction without further purification. The crude product: 1.94 g.

1.94 g of (E)-3-[4-(methoxymethoxy)phenyl]-N-(3-pyridylmethyl)-2-buteneamide was dissolved in 38 ml methanol and stirred with 1.9 ml of concentrated hydrochloric acid at room temperature for 8 hours. The reaction mixture was extracted with ethyl acetate and water, and the aqueous layer was further extracted with ethyl acetate. The combined ethyl acetate layers were washed with water and brine, and dried over anhydrous magnesium sulfate. The drying agent was filtered off and the solvent was evaporated to give a residue, which was then recrystallized from ethyl acetate/n-hexane to provide (E)-3-(4-hydroxyphenyl)-N-(3-pyridylmethyl)-2-buteneamide (1.16 g, 96.5% after 2 steps).

0.54 g of (E)-3-(4-hydroxyphenyl)-N-(3-pyridylmethyl)-2-buteneamide was dissolved in 221 1 dimethylformamide and mixed with 0.332 g of anhydrous potassium carbonate, and subsequently with 0.26 ml ethyl chloroacetate at room temperature under a stream of argon. After reacting for 5 hours, the reaction mixture was extracted with ethyl acetate and water, and the aqueous layer was further extracted with ethyl acetate. The combined ethyl acetate layers were washed with water and brine, and dried over anhydrous magnesium sulfate. The drying agent was filtered off and the filtrate was evaporated and purified via column chromatography on silica gel (ethyl acetate:methanol=10:1) to give a reaction product (0.554 g, 78.2%). The reaction product was recrystallized from ethyl acetate/hexane to provide ethyl [4-[(E)-1-methyl-2-[N-(3-pyridylmethyl)carbamoyl] ethenyl]phenoxy]acetate (88 mg, 16.2%).

Properties: a pale yellow solid; $^1$H-NMR(CDCl$_3$) δ: 1.31 (3H, t, J=7.2 Hz), 2.57 (3H, s), 4.28 (2H, q, J=7.2 Hz), 4.55 (2H, d, J=5.9 Hz), 4.64 (2H, s), 6.00 (2H, brs), 6.88 (2H, d, J=8.9 Hz), 7.28 (1H, m), 7.40 (2H, d, J=8.9 Hz), 7.70 (1H, m), 8.54 (1H, m), 8.57 (1H, d, J=1.7 Hz).

EXAMPLE 86

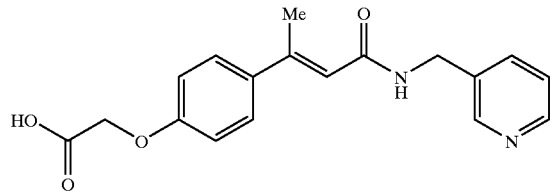

0.5 g of ethyl [4-[(E)-1-methyl-2-[N-(3-pyridylmethyl) carbamoyl]ethenyl]-phenoxy]acetate from Example 85 was mixed with 0.39 g of anhydrous potassium carbonate and 20 ml of 50% aqueous methanol, and then refluxed for 2 hours. The reaction mixture was adjusted to pH 6 with 3 mol/l HCl while cooling on ice, and the precipitate was filtered and dried to give [4-[(E)-1-methyl-2-[N-(3-pyridylmethyl) carbamoyl]ethenyl]phenoxy]acetic acid (179.6 mg, 39%).

Properties: mp 228–229° C. (ethyl acetate/hexane); $^1$H-NMR(DMSO-d$_6$) δ: 2.47 (3H, d), 4.37 (2H, d, J=5.8 Hz), 4.71 (2H, s), 6.22 (1H, d), 6.94 (2H, d, J=8.8 Hz), 7.37 (1H, m), 7.45 (2H, d, J=8.8 Hz), 7.68 (1H, m), 7.47 (1H, dd, J=8.9 Hz, J=4.8 Hz), 7.85 (2H, m), 13.07 (1H, brs).

EXAMPLE 87

Synthesis of [4-[1-Phenyl-2-[N-(3-pyridylmethyl) carbamoyl]ethenyl]phenoxy]acetic Acid

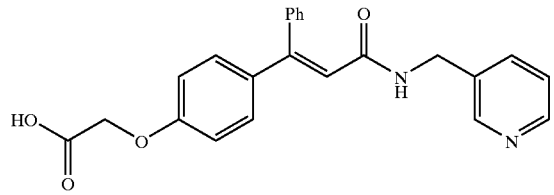

2 g of 4-hydroxybenzophenone was dissolved in 20 ml dichloromethane and 2.12 ml diisopropylamine, and then stirred with 0.9 ml chloromethyl methyl ether at room temperature for 16 hours. Dichloromethane and water were added to the reaction mixture, which was then extracted with dichloromethane three times, washed with saturated aqueous sodium bicarbonate and brine, and then dried over anhydrous magnesium sulfate. The drying agent was filtered off and the solvent was evaporated to give 4-(methoxymethoxy) benzophenone as an oil quantitatively. Yield: 2.44 g.

0.485 g of 4-(methoxymethoxy)benzophenone was dissolved in 0.45 ml ethyl bromoacetate, 1.5 ml benzene and 1.5 ml toluene, mixed with 3.27 g of zinc and 50 mg of iodine, and then refluxed for 2 hours under a stream of argon. The reaction mixture was mixed with water, adjusted to pH 1 with concentrated sulfuric acid, and then extracted with benzene three times. The extract was filtrated to remove insoluble components, washed twice with water and once with brine, followed by drying over anhydrous magnesium sulfate. The drying agent was filtered off and the filtrate was evaporated and purified via column chromatography on silica gel (ethyl acetate:hexane=1:5) to give ethyl 3-hydroxy-3-[4-(methoxymethoxy)phenyl]-3-phenylpropionate (263 mg, yield: 39.9%) as an oil.

0.23 g of ethyl 3-hydroxy-3-[4-(methoxymethoxy) phenyl]-3-phenylpropionate was dissolved in 1 ml ethanol, and then stirred with 14 ml of 2 mol/l aqueous sodium hydroxide at room temperature for 16 hours. The reaction mixture was adjusted to pH 1 with concentrated hydrochloric acid, extracted with ethyl acetate three times, washed twice with water and once with brine, followed by drying over anhydrous magnesium sulfate. The drying agent was filtered off and the solvent was evaporated to give 3-hydroxy-3-[4-(methoxymethoxy)phenyl]-3-phenylpropionic acid (202 mg, yield: 95.7%) as a white solid.

0.66 g of 3-hydroxy-3-[4-(methoxymethoxy)phenyl]-3-phenylpropionic acid was mixed with anhydrous pyridine, and subsequently with 1.65 ml phosphorus oxychloride on ice under a stream of argon. After 4 hour stirring at room temperature, water saturated with ethyl acetate was slowly added dropwise to the reaction mixture. The reaction mixture was then mixed with water, extracted with ethyl acetate three times, washed twice with water and once with brine, followed by drying over anhydrous magnesium sulfate. The dying agent was filtered off and the solvent was evaporated to give a crude product, which was used for the subsequent reaction without further purification. The crude product was dissolved in dimethylformamide, and then stirred with 0.34 ml 3-(aminomethyl)pyridine, 0.55 ml diethyl cyanophosphate and 0.45 ml triethylamine for 4 hours under a stream of argon. After addition of ethyl acetate and water, the reaction mixture was extracted with ethyl acetate three times, washed twice with water and once with brine, followed by drying over anhydrous magnesium sulfate. The drying agent was filtered off and the filtrate was evaporated and purified via column chromatography on silica gel (chloroform:methanol=15:1) to give a product (495 mg) as an oil. The product was dissolved in 6 ml methanol without further purification, stirred with 0.34 ml of concentrated hydrochloric acid for 48 hours, extracted with ethyl acetate, washed twice with water and once with brine, followed by drying over anhydrous magnesium sulfate. The drying agent was filtered off and the filtrate was evaporated and purified via column chromatography on silica gel (chloroform:methanol=20:1) to give 3-(4-hydroxyphenyl)-3-phenyl-N-(3-pyridylmethyl)acrylamide (106 mg, yield: 14.2%) as a white solid.

95 mg of 3-(4-hydroxyphenyl)-3-phenyl-N-(3-pyridylmethyl)acrylamide was reacted with 2 ml of dimethylformamide, 48 mg of anhydrous potassium carbonate and 0.04 ml of ethyl chlorocarbonate for 4 hours under a stream of argon. The reaction mixture was extracted with ethyl acetate three times, washed twice with water and once with brine, and then dried over anhydrous magnesium sulfate. The drying agent was filtered off and the filtrate was evaporated and purified via column chromatography on silica gel (chloroform:methanol=20:1) to give ethyl [4-[1-phenyl-2-[N-(3-pyridylmethyl)carbamoyl]ethenyl] phenoxy]acetate (140 mg, yield: 100%) as an oil.

100 mg of ethyl [4-[1-phenyl-2-[N-(3-pyridylmethyl) carbamoyl]ethenyl]phenoxy]acetate was mixed with 66 mg of potassium carbonate and 10 ml of 50% aqueous methanol, and then refluxed for 2 hours. The reaction mixture was adjusted to pH 6 with 3 mol/l hydrochloric acid, extracted with ethyl acetate, washed twice with water and once with brine, followed by drying over anhydrous magnesium sulfate. The drying agent was filtered off and the solvent was evaporated to give crude crystals (100 mg), which were then recrystallized from ethyl acetate to provide [4-[1-phenyl-2-[-(3-pyridylmethyl)carbamoyl]ethenyl]phenoxy]acetic acid (80 mg, yield: 86.7%) as a white solid.

Properties: mp 187–189° C. (ethyl acetate); $^1$H-NMR (DMSO-$d_6$) δ: 4.05 (2H, s), 4.22 (2H, d, J=5.8 Hz), 6.40 (1H, s), 6.73 (2H, d, J=8.8 Hz), 7.06 (2H, d, J=8.8 Hz), 7.11 (2H, m), 7.27–7.45 (4H, m), 7.46–7.50 (1H, m), 8.39 (1H, d, J=1.7 Hz), 8.41–8.48 (1H, m), 8.53 (1H, d, J=9.4 Hz).

EXAMPLE 88

Synthesis of [[4-[(E)-2-[N-(3-Pyridylmethyl) carbamoyl]ethenyl]phenyl]amino]acetic Acid

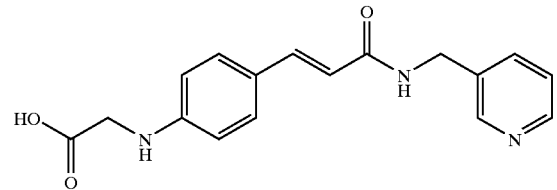

A solution of 4-aminocinnamic acid (1.88 g), ethyl trifluoroacetate (6.8 ml) and triethylamine (4.8 ml) in 20 ml methanol was stirred at room temperature for 4 hours, and 0.3 mol/l hydrochloric acid was added thereto, on ice, to precipitate a solid, which was then filtered, washed with water, and then dried by heating under reduced pressure to give 4-(trifluoroacetylamino)cinnamic acid (2.81 g, 94%).

A solution of 4-(trifluoroacetylamino)cinnamic acid (1.30 g) and 3-(aminomethyl)pyridine (540 mg) in 20 ml dimethylformamide was mixed with 0.9 ml diethyl cyanophosphate and subsequently with 0.8 ml triethylamine on ice, and then stirred at room temperature for 4 hours. The solid precipitated from water was then filtered, washed with water, and dried by heating under reduced pressure to give N-(3-pyridylmethyl)-4-[(trifluoroacetyl)amino]cinnamamide (1.61 g, 92%).

A suspension of N-(3-pyridylmethyl)-4-[(trifluoroacetyl) amino]cinnamic acid (1.55 g) and potassium carbonate (1.84 g) in 10 ml dimethylformamide was stirred with 0.7 ml t-butyl bromoacetate for 24 hours. After removal of inorganic salts by filtration, insoluble components precipitated from water were filtered off. The filtrate was extracted with ethyl acetate and the organic layer was washed with water and brine, and then dried over magnesium sulfate. The drying agent was filtered off and the solvent was evaporated to give a residue, which was then separated and purified via column chromatography on silica gel (chloroform:methanol=50:1) to provide t-butyl [[4-[(E)-2-[N-(3-pyridylmethyl)carbamoyl]ethenyl]phenyl] (trifluoroacetyl)amino]acetate (582 mg, 30%).

A solution of t-butyl [[4-[(E)-2-[N-(3-pyridylmethyl) carbamoyl]ethenyl]-phenyl](trifluoroacetyl)amino]acetate (580 mg) in aqueous methanol was mixed with 74 mg of sodium hydroxide, and then stirred at room temperature for 24 hours and subsequently at 60° C. for 1 hour. After evaporation of methanol, the reaction mixture was mixed with 0.4 ml of 2 mol/l hydrochloric acid, and extracted with ethyl acetate. The organic layer was dried over sodium sulfate. The drying agent was filtered off and the solvent was evaporated to precipitate a solid, which was then washed with methanol/ethyl acetate and dried by heating under reduced pressure to provide [[4-[(E)-2-[N-(3-pyridylmethyl) carbamoyl]ethenyl]phenyl]amino]acetic acid of interest (78 mg, 20%) as a pale yellow solid.

Properties: solid; $^1$H-NMR(DMSO-$d_6$) δ: 3.84 (2H, s), 4.40 (2H, d, J=5.8 Hz), 6.36 (1H, d, J=15.7 Hz), 6.57 (2H, d, J=8.6 Hz), 7.29–7.38 (4H, m), 7.65–7.71 (1H, m), 8.44–8.51 (3H, m).

EXAMPLE 89

Synthesis of [[4-[(E)-2[-N-(3-Pyridylmethyl) carbamoyl]ethenyl]phenyl]thio]acetic Acid

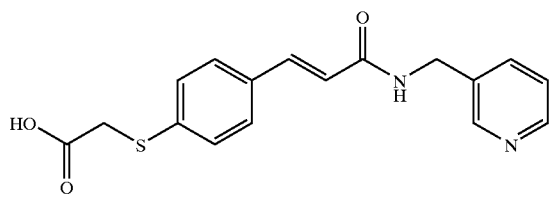

1.36 g of potassium hydroxide was dissolved in 38 ml ethanol by heating, allowed to cool, mixed with 3.8 g of 4-bromobenzenethiol, further with 3.8 g of silica gel and 2.96 ml of t-butyl bromoacetate, followed by stirring at room temperature for 4 hours. Silica gel was filtered off and the filtrate was concentrated and purified via column chromatography on silica gel (ethyl acetate:hexane=1:20) to give t-butyl [(4-bromophenyl)thio]acetate (5.98 g, 98.6%).

3.46 g of t-butyl [(4-bromophenyl)thio]acetate was mixed with 8 ml diisopropylethylamine, 0.6 g of triphenylphosphine, 5.2 ml ethyl acrylate and 35 ml acetonitrile to form a solution. 0.26 g of palladium acetate was further added to the solution and refluxed under a stream of argon for 44 hours. The reaction mixture was extracted with ethyl acetate, washed with water. The aqueous layer was further extracted with ethyl acetate. The combined ethyl acetate layers were washed with water and brine, and then dried over anhydrous magnesium sulfate. The drying agent was filtered off and the filtrate was concentrated and purified via column chromatography on silica gel (ethyl acetate:hexane=1:20) to give ethyl 4-[[(t-butoxycarbonyl) methyl]thio]cinnamate (2.7 g, 73.7%).

389 mg of ethyl 4-[[(t-butoxycarbonyl)methyl]thio] cinnamate was mixed with 10 ml of 50% aqueous methanol and 167 mg of potassium carbonate, and then refluxed for 1 hour. After allowing to cool, the reaction solvent was concentrated and dried in a vacuum desiccator for 2 hours. The dried product was suspended in 10 ml dimethylformamide and mixed with 0.19 ml 3-(aminomethyl)pyridine, 0.31 ml diethyl cyanophosphate and 0.26 ml triethylamine in this order under a stream of argon, followed by stirring at room temperature for 3 hours. The reaction mixture was extracted with ethyl acetate and water. The aqueous layer was further extracted with ethyl acetate. The combined ethyl acetate layers were washed with water and brine, and then dried over anhydrous magnesium sulfate. The drying agent was filtered off, and the filtrate was concentrated to give a residue, which was then dissolved in 10 ml dichloromethane and stirred with 0.71 ml trifluoroacetic acid at room temperature for 16 hours. The reaction mixture was concentrated and purified via column chromatography on silica gel (chloroform:methanol=5:1). Purification via column chromatography on silica gel (ethyl acetate:methanol=2:1) was repeated to give [[4-[(E)-2-[N-(3-pyridylmethyl)carbamoyl] ethenyl]phenyl]thio]acetic acid (94.6 mg, 23.8% after 3 steps).

Properties: mp 160–161° C. (ethyl acetate/hexane); $^1$H-NMR(DMSO-$d_6$) δ: 3.88 (2H, s), 4.50 (2H, d, J=5.8 Hz), 6.67 (1H, d, J=15.8 Hz), 7.34 (2H, d, J=8.3 Hz), 7.44 (1H, d, J=15.8 Hz), 7.53 (2H, d, J=8.3 Hz), 7.70 (1H, m), 8.05 (1H, d, J=8.4 Hz), 8.66 (2H, m), 8.86 (1H, q, J=5.6 Hz).

EXAMPLE 90

Regulatory Effects on Interleukins

C57BL/6CrSlc male mice were intraperitoneally injected with 2.0 ml of 3% Brewer tioglycolate medium. Three days later, macrophages were collected from the abdominal cavity with 5.0 ml Hank's balanced salt solution, and then equally divided into each well of a 48-well plate using RPMI 1640 medium supplemented with 10% FBS (Fetal Bovine Serum), followed by incubation in a $CO_2$ incubator for 1 hour. After the macrophages adhered to the walls of the plate, they were incubated for 48 hours in the presence of a test compound with different concentrations. Following the incubation, the supernatant was collected from each well, assayed for IL-6, IL-10 and L-12 by ELISA to determine inhibitory rates against the production of these interleukins. The results are shown in Table 1.

TABLE 1

| Example No. | Concentration (μg/ml) | Inhibitory rate (%) | | |
|---|---|---|---|---|
| | | IL-10 | IL-12 | IL-6 |
| 1 | 1 | 2.1 | 32.4 | 29.3 |
| | 5 | 29.1 | 39.5 | 34.5 |
| | 10 | 23.7 | 64.6 | 40.4 |
| 2 | 10 | 27.8 | 35.0 | 58.8 |
| | 50 | 51.4 | 63.8 | 78.9 |
| | 100 | 50.0 | 65.4 | 88.0 |
| 7 | 1 | 17.9 | 28.4 | 13.5 |
| | 5 | 1.3 | 40.1 | 31.5 |
| | 10 | 25.4 | 52.5 | 32.5 |
| 10 | 10 | 29.5 | 30.3 | 61.2 |
| | 50 | 33.3 | 27.8 | 63.5 |
| | 100 | 27.8 | 35.0 | 61.6 |
| 16 | 1 | 49.9 | 31.4 | 26.1 |
| | 5 | 50.1 | 47.4 | 41.3 |
| | 10 | 34.9 | 40.3 | 79.0 |
| 29 | 10 | −25.7 | 37.6 | −9.5 |
| 30 | 10 | −38.9 | 71.7 | 58.8 |
| 36 | 10 | −45.8 | 52.1 | 53.1 |
| | 50 | −13.0 | 82.1 | 56.7 |
| | 100 | 22.2 | 64.0 | 21.7 |
| 74 | 10 μM/L | — | 51.1 | — |
| 75* | 10 μM/L | — | 42.2 | — |
| 76 | 10 μM/L | — | 50.0 | — |
| 78 | 10 μM/L | — | 49.2 | — |
| 79 | 10 μM/L | — | 43.0 | — |
| 80 | 10 μM/L | — | 52.3 | — |
| 81 | 10 μM/L | — | 41.0 | — |
| 82 | 10 μM/L | — | 30.7 | — |
| 83 | 10 μM/L | — | 40.9 | — |
| 84 | 10 μM/L | — | 38.9 | — |
| 85 | 10 μM/L | — | 47.4 | — |
| 86 | 10 μM/L | — | 48.4 | — |

TABLE 1-continued

| Example No. | Concentration (μg/ml) | Inhibitory rate (%) | | |
|---|---|---|---|---|
| | | IL-10 | IL-12 | IL-6 |
| 88 | 10 μM/L | — | 26.4 | — |
| 89 | 10 μM/L | — | 51.1 | — |

75*: methyl 3-[4-[(E)-2-[N-(3-pyridylmethyl)carbamoyl]ethenyl]phenyl]propionate

EXAMPLE 91

Inhibitory Effects on Urinary Proteins in Rats with Minimal Change Nephrosis

Six week old S.D. male rats were intravenously injected with Puromycin Aminonucleoside (PA; SIGMA)at a dose of 50 mg/kg so as to develop nephrosis. Six days after PA treatment, the rats were administered with a test drug at a dose of 2 mg/kg/day by day 11. Each rat was assayed for an excreted urinary protein level at day 11 to determine an inhibitory rate. The results are shown in Table 2.

TABLE 2

| Example No. | Inhibitory rate (%) |
|---|---|
| 1 | 41 |
| 7 | 50 |
| 10 | 56 |
| 16 | 42 |
| 36 | 29 |

EXAMPLE 92

Inhibitory Effect on Thromboxane $A_2$ Synthase

Eight week old Sprague-Dawley male rats were used in this example. The rats were anesthetized with pentobarbital sodium. The blood was collected from the abdominal aorta using a heparinized syringe, and centrifuged at 1,300 rpm for 7 minutes to obtain platelet rich plasma (PRP). PRP was suspended in an equivalent volume of a buffer containing 25 mmol/l Tris-HCl, 130 mmol/l sodium chloride and 0.3 mmol/l EDTA (pH 7.4)(buffer A), followed by centrifugation at 4° C., at 1,500 rpm for 5 minutes. This procedure was repeated twice, and PRP was finally suspended in a buffer containing 25 mmol/l Tris-HCl, 130 mmol/l, 0.1% glucose and 0.1% albumin (pH7.4)(buffer B).

$5 \times 10^6$ cells/mm$^3$ PRP preparation in buffer B was divided into each well of a 96-well plate in an amount of 150 μl/well. Each test substance was prepared at a final concentration of 10 μmol/l and added to the PRP preparation in an amount of 50 μl/well. Immediately after addition of the test substance, 5 μl of an aggregation-inducing agent, type IV collagen (1 mg/ml) or arachidonic acid (50 mmol/l), was added and incubated for 10 minutes. 20 μl of an EDTA-indomethacin solution was added to the each well to stop the reaction. The supernatant was assayed for thromboxane $B_2$ ($TXB_2$), stable metabolite of thromboxane $A_2$ ($TXA_2$), using a $TXB_2$ measurement kit (Cayman). The results are shown in Table 3.

TABLE 3

| Example No. | $TXB_2$ induced by collagen (Inhibitory rate; %) | $TXB_2$ induced by arachidonic acid (Inhibitory rate; %) |
|---|---|---|
| 1 | 32 | 67 |
| 37 | 26 | 26 |
| 41 | 14 | 36 |
| 53 | 43 | 56 |
| 65 | 12 | 23 |
| 72 | 46 | 61 |
| 73 | 47 | 23 |

A compound with an inhibitory rate of 20% or more was identified as positive. All of the test compounds shown in Table 3 had inhibitory activity against $TXA_2$ production mediated by collagen or arachidonate, indicating that these compounds may inhibit thromboxane $A_2$ synthase. In particular, each compound from Examples 1, 53 and 72 showed a strong inhibitory activity of 50% or more.

All publications, patents and patent applications cited herein are incorporated herein by reference in their entirety.

INDUSTRIAL APPLICABILITY

The present invention provides novel cinnamamide derivatives useful as an immunomodulatory agent and/or a prophylactic or therapeutic agent for nephrotic syndrome, circulatory disorders or respiratory diseases.

What is claimed is:

1. A cinnamamide compound having the following formula (I):

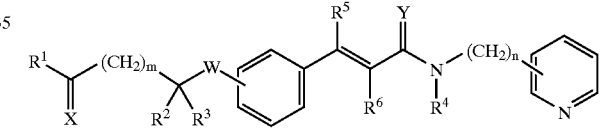

(I)

wherein

R$^1$ represents a hydroxyl group, a C$_{1-6}$-alkoxy group, an arylalkoxy group or a substituted or unsubstituted amino group;

R$^2$ and R$^3$ are same or different, each of which represents a hydrogen atom, a halogen atom or a C$_{1-4}$-alkyl group;

R$^4$ represents a hydrogen atom or a C$_{1-6}$-alkyl group;

R$^1$ represents a hydrogen atom, a C$_{1-6}$-alkyl group or an aryl group;

R$^6$ represents a hydrogen atom, a C$_{1-6}$-alkyl group, a cyano group or a C$_{1-6}$-alkoxy-carbonyl group;

W represents an oxygen atom, a sulfur atom, an imino group, a methylene group, a hydroxymethylene group or a carbonyl group;

X and Y are same or different, each of which represents an oxygen atom or a sulfur atom;

m represents an integer of 0 to 2;

n represents an integer of 1 to 3; and when m is 0, a group: —C(R$^2$)(R$^3$)—W— may represent a vinylene group;

or a pharmaceutically acceptable salt thereof.

2. The cinnamamide compound or pharmaceutically acceptable salt thereof according to claim 1, wherein the substituted amino group mentioned for R$^1$ is substituted with one or two groups selected from a substituted or unsubstituted $C_{1-6}$-alkyl group, a substituted or unsubstituted $C_{3-6}$-cycloalkyl group, a substituted or unsubstituted $C_{1-6}$alkoxy group and a hydroxyl group; or is a cyclic amino group.

3. A pharmaceutical composition, which comprises as an active ingredient the cinnamamide compound or pharmaceutically acceptable salt thereof according to claim 1.

4. A method of modulating an immune response in a subject in need thereof, comprising administering to the subject an effective amount of the cinnamamide compound or pharmaceutically acceptable salt thereof according to claim 1.

5. A method of treating or preventing nephrotic syndrome in a subject in need thereof, comprising administering to the subject an effective amount of the cinnamamide compound or pharmaceutically acceptable salt thereof according to claim 1.

6. A method of treating or preventing circulatory disorders in a subject in need thereof, comprising administering to the subject an effective amount of the cinnamamide compound or pharmaceutically acceptable salt thereof according to claim 1.

7. A method of treating or preventing respiratory diseases in a subject in need thereof, comprising administering to the subject an effective amount of the cinnamamide compound or pharmaceutically acceptable salt thereof according to claim 1.

8. The cinnamamide compound or pharmaceutically acceptable salt thereof according to claim 1, wherein $R^1$ is a hydroxyl group or a substituted or unsubstituted amino group; at least one of $R^2$ and $R^3$ is a halogen atom; $R^5$ is a hydrogen atom, a $C_{1-6}$-alkyl group or an aryl group; when $R^5$ is a hydrogen atom, $R^6$ is a $C_{1-6}$-alkyl group, a cyano group or a $C_{1-6}$-alkoxy-carbonyl group, and at least one of X and Y is are a sulfur atom.

9. A cinnamamide compound having the following formula (Ia):

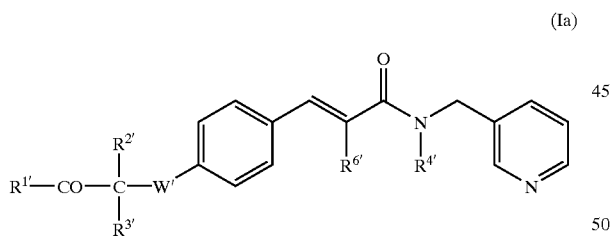

wherein
$R^{1'}$ represents a hydroxyl group, a methoxy group or an ethoxy group;
$R^{2'}$ and $R^{3'}$ are same or different, each of which represents a hydrogen atom or a fluorine atom;
$R^{4'}$ represents a hydrogen atom or a methyl group;
$R^{6'}$ represents a hydrogen atom or a cyano group; and
$W'$ represents an oxygen atom, a sulfur atom or a methylene group;
or a pharmaceutically acceptable salt thereof.

10. The cinnamamide compound or pharmaceutically acceptable salt thereof according to claim 9, which is a compound having the formula:

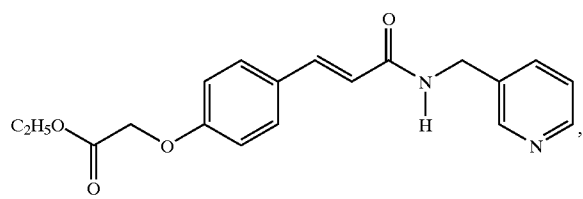

the formula:

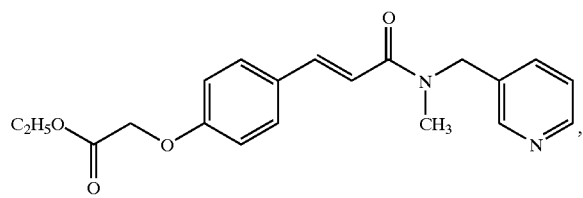

the formula:

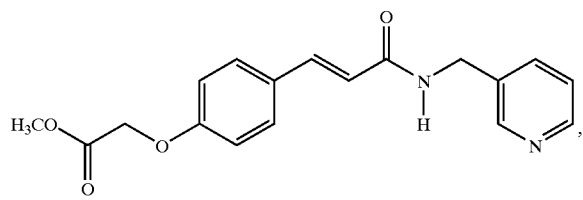

the formula:

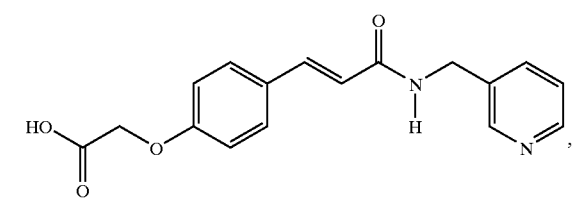

the formula:

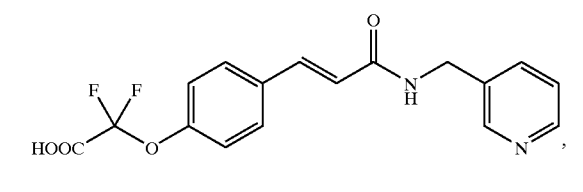

the formula:

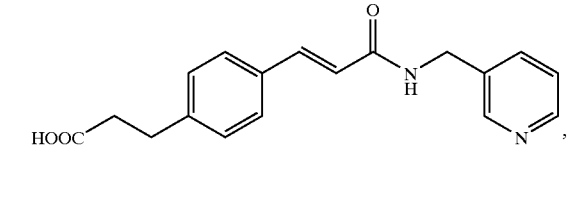

the formula:
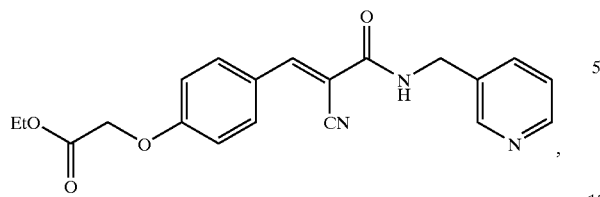
the formula:
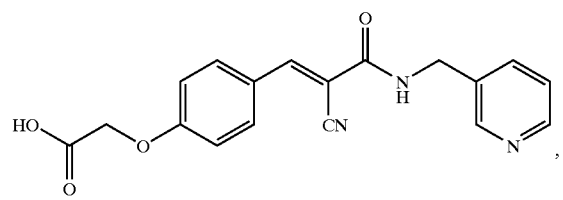
the formula:
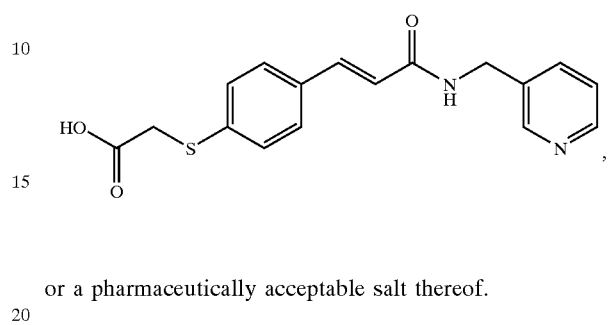
or a pharmaceutically acceptable salt thereof.
* * * * *